US005783600A

United States Patent [19]

Bisgaier et al.

[11] Patent Number: 5,783,600
[45] Date of Patent: Jul. 21, 1998

[54] CARBOXYALKYLETHERS, FORMULATIONS, AND TREATMENT OF VASCULAR DISEASES

[75] Inventors: Charles Larry Bisgaier; Paul Leroy Creger; Alan Robert Saltiel, all of Ann Arbor; Sherrie Rae Tafuri, Dexter, all of Mich.

[73] Assignee: Warner-Lambert Company, Morris Plains, N.J.

[21] Appl. No.: 806,580

[22] Filed: Feb. 25, 1997

Related U.S. Application Data

[62] Division of Ser. No. 409,780, Mar. 24, 1995, Pat. No. 5,648,387.

[51] Int. Cl.⁶ .................................. A61K 31/225
[52] U.S. Cl. .................. 514/547; 514/381; 514/529; 514/531; 514/535; 514/544; 514/546; 514/557; 514/571; 514/572; 514/573; 514/574; 514/693; 514/699
[58] Field of Search ................... 560/181, 118, 560/60, 180, 177; 562/470, 500, 582, 577; 568/442, 494; 548/253; 514/381, 529, 530, 531, 533, 547, 571, 572, 573, 574, 544, 557, 693, 699

[56] References Cited

U.S. PATENT DOCUMENTS

| 3,320,079 | 5/1967 | Perry et al. | 106/181 |
|---|---|---|---|
| 3,674,836 | 7/1972 | Creger | 260/473 |
| 3,703,549 | 11/1972 | Yeomans | 260/533 A |
| 3,742,068 | 6/1973 | Moersch et al. | 41/10 |
| 3,930,024 | 12/1975 | Creger | 424/343 |
| 4,454,145 | 6/1984 | Cristofori et al. | 424/266 |
| 4,711,896 | 12/1987 | Bar-Tana et al. | 514/570 |
| 4,990,227 | 2/1991 | Steiniger et al. | 204/59 R |

OTHER PUBLICATIONS

*Lipids*, vol. 12, No. 1, 1976, Blumenthal et al., pp. 44–48.
*Diabetes*, vol. 37, 1988, Tzur et al., pp. 1618–1624.
*Supplement to Circulation*, vol. 84, No. 4, 1991, Jones et al., Abstract 1925.
*Current Therapeutic Research*, vol. 49, No. 4, 1991, Bimmermann et al., pp. 635–643.
*Antilipidemic Drugs, Medicinal, Chemical and Biochemical Aspects*, Elsevier Science Publishers B.V., Amsterdam, Witiak D.T. et al. (Editors), Chapter 8, Roth et al., pp. 225–255 (1960).
*J. Clin. Invest.*, vol. 95, 1995, Staels et al., pp. 705–712.
*Endocrinology*, vol. 133, No. 1, 1993, Sandouk et al., pp. 352–359.
*The Journal of Biological Chemistry*, vol. 260, No. 5, 1985, Frost et al., pp. 2646–2652.

*Primary Examiner*—Michael L. Shippen
*Attorney, Agent, or Firm*—Charles W. Ashbrook

[57] ABSTRACT

Dialkyl ethers lower Lp(a) and triglycerides, and elevate HDL-cholesterol, and are thereby useful for treating vascular diseases and noninsulin-dependent diabetes mellitus.

8 Claims, 23 Drawing Sheets

PD 72953

| $Y_1 \diagdown \diagup -(CH_2)_n - O - (CH_2)_m - \diagdown \diagup Y_2$ | | | | | | | |
|---|---|---|---|---|---|---|---|
| EXAMPLE | 1 | 4 | 6 | 7 | 2 | 9 | 8 |
| IN FIGURE | A | B | C | D | E | F | G |
| n | 4 | 2 | 3 | 4 | 5 | 3 | 6 |
| m | 4 | 2 | 3 | 4 | 5 | 5 | 6 |
| $Y_1$ | COOH | COOH | COOEt | COOEt | COOH | COOH | COOCH$_3$ |
| $Y_2$ | COOH | COOH | COOEt | COOEt | COOH | COOH | COOCH$_3$ |

CARBOXYALKYLETHERS, FORMULATIONS, AND TREATMENT OF VASCULAR DISEASES

This application is a division of application Ser. No. 08/409,780 filed Mar. 24, 1995 now U.S. Pat. No. 5,648,387.

FIELD OF THE INVENTION

This invention relates to compounds which are dialkyl ethers having terminal carboxy or tetrazole groups. The compounds are useful for lowering certain plasma lipids in animals, including Lp(a), triglycerides, VLDL-cholesterol, and LDL-cholesterol, and elevating others such as HDL-cholesterol. The compounds are effective for preventing and treating vascular diseases and diabetes, for example, by increasing insulin sensitivity.

BACKGROUND OF THE INVENTION

Vascular diseases such as coronary heart disease, stroke, restenosis, and peripheral vascular disease, remain the leading cause of death and disability throughout the world. About 1.5 million people die each year in the U.S. alone from myocardial infarction resulting from congestive heart failure. While diet and life style can accelerate the onset of vascular diseases, genetic predisposition leading to dyslipidemia is a significant factor in vascular-related disabilities and deaths. "Dyslipidemia" means abnormal levels of lipoproteins in blood plasma.

Several risk factors have been associated with increased risk of vascular disease. Among these are the dyslipidemias of high levels of low-density lipoprotein (LDL), and low levels of high-density lipoproteins (HDL). The ratio of HDL-cholesterol to LDL-cholesterol is often used to assess the risk of vascular disease. A high ratio of HDL/LDL cholesterol is desirable. Compounds that increase this ratio by either lowering LDL or increasing HDL, or both, therefore are beneficial. Recent studies have shown that elevated levels of a modified form of LDL called lipoprotein(a), "Lp(a)", are detrimental.

Lp(a)-cholesterol appears to be undesirable, since elevated levels of Lp(a) have been associated with the development of atherosclerosis, coronary heart disease, myocardial infarction, stroke, cerebral infarction, and restenosis following balloon angioplasty. In fact, Lp(a) appears to be an excellent predictor for stroke. Accordingly, high concentrations of cholesterol in the form of Lp(a) is one of the major risk factors leading to death from heart disease.

We have now discovered that certain ethers are effective in lowering plasma concentrations of Lp(a). This invention thus provides a method for lowering plasma levels of Lp(a) comprising administering a dialkanoic ether or ester thereof. These types of compounds have not heretofore been utilized to treat vascular disease. For example, U.S. Pat. No. 3,320,079 discloses 3,3'-oxybis (2,2-dimethylpropionic acid) as a plasticizer. U.S. Pat. No. 3,930,024 discloses a series of alkanediols which are said to lower serum triglycerides. U.S. Pat. No. 3,674,836 discloses phenoxy alkanoic acids which are said to reduce triglycerides. U.S. Pat. No. 4,711,896 discloses certain α,ω-dicarboxylic acids which are said to lower lipids.

An object of this invention is to provide a series of carboxy substituted dialkyl ethers which are effective in lowering plasma Lp(a). A further object is to provide pharmaceutical formulations containing the compounds, and a method for treating vascular disease utilizing the compounds.

SUMMARY OF THE INVENTION

This invention provides new chemical entities characterized as carboxy or tetrazole substituted dialkyl ethers, and the salts and esters thereof. The invention more particularly provides compounds defined by Formula I

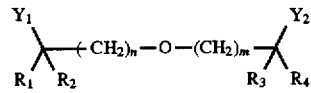

wherein n and m independently are integers from 2 to 9;

$R_1$, $R_2$, $R_3$, and $R_4$ independently are $C_1$–$C_6$ alkyl, $C_2$–$C_6$ alkenyl, $C_2$–$C_6$ alkynyl, and $R_1$, and $R_2$ together with the carbon to which they are attached, and $R_3$ and $R_4$ together with the carbon to which they are attached, can complete a carbocyclic ring having from 3 to 6 carbons, $Y_1$ and $Y_2$ independently are COOH, CHO, tetrazole, and $COOR_5$ where $R_5$ is $C_1$–$C_6$ alkyl, $C_2$–$C_6$ alkenyl, $C_2$–$C_6$ alkynyl;

and where the alkyl, alkenyl, and alkynyl groups may be substituted with one or two groups selected from halo, hydroxy, $C_1$–$C_6$ alkoxy, and phenyl.

Preferred compounds of the invention have the above formula wherein n and m are the same integer, and wherein $R_1$, $R_2$, $R_3$, and $R_4$ each are alkyl.

Further preferred are compounds wherein $Y_1$ and $Y_2$ independently are COOH or $COOR_5$ where $R_5$ is alkyl.

The most preferred compounds of the invention have the formula

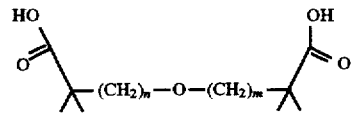

wherein n and m are each an integer selected from 2, 3, 4, or 5, ideally 4 or 5.

An especially preferred compound has the formula

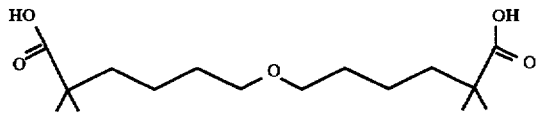

Also provided are the pharmaceutically acceptable salts of the acids of the invention.

A further embodiment of the invention are pharmaceutical formulations comprising a compound of Formula I together with a pharmaceutically acceptable carrier, diluent, or excipient therefor.

Also provided by the invention are methods for treating vascular diseases such as peripheral vascular disease, coronary heart disease, stroke, and restenosis. The invention provides a method for lowering Lp(a), plasma triglycerides, very low-density lipoprotein (VLDL) cholesterol, low-density lipoprotein (LDL) cholesterol, and apolipoprotein B. The invention additionally provides a method for elevating plasma high-density lipoprotein (HDL) cholesterol, apolipoprotein A-I, and apolipoprotein E. The invention also provides a method for treating and preventing noninsulin-dependent diabetes mellitus by increasing insulin sensitivity by administering a compound of Formula I.

DETAILED DESCRIPTION OF THE INVENTION

The compounds of this invention will be named as alkanoic acids and esters. For example, the compound of the formula

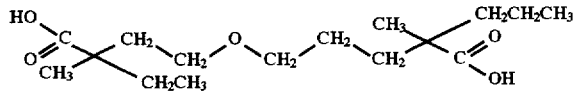

will be named as a pentanoic acid, specifically 2-methyl-2-n-propyl-5-(3-methyl-3-hydroxy-carbonyl)-pentoxy pentanoic acid. As noted above, preferred compounds are those wherein n and m in Formula I are the same, and $R_1$, $R_2$, $R_3$, and $R_4$ are all the same alkyl group. When $Y_1$ and $Y_2$ both are carboxy groups, the compounds will be named as oxybis alkanoic acids. For example, a preferred compound of the formula

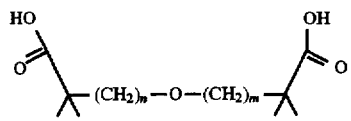

where n and m both are 4, can be named 6,6'-oxybis (2,2-dimethylhexanoic acid).

In Formula I, $R_1$, $R_2$, $R_3$, and $R_4$ are defined to include "$C_1$–$C_6$ alkyl", which term includes methyl, ethyl, isopropyl, tert-butyl, n-hexyl, and 2-methyl-pentyl. The alkyl group can be substituted with halo, hydroxy, $C_1$–$C_6$ alkoxy, and phenyl. "Halo" includes chloro, bromo, and iodo. "$C_1$–$C_6$ alkoxy" is a $C_1$–$C_6$ alkyl group linked through oxygen, such as ethoxy, isopropoxy, n-hexyloxy, and the like. Typical substituted alkyl groups are chlormethyl, 3-hydroxy-hexyl, 4-phenylbutyl, 2-iodopentyl, isopropoxymethyl, and the like.

$R_1$, $R_2$, $R_3$, and $R_4$ also can include $C_2$–$C_6$ alkenyl and substituted alkenyl and $C_2$–$C_2$ alkynyl and substituted alkynyl. Typical groups include vinyl, 2-propenyl, 3-chloro-4-hexenyl, 2-phenyl-3-pentenyl, ethynyl, 2-methoxyethynyl, 2-bromoethynyl, 6-phenyl-3-hexynyl, and the like.

$R_1$ and $R_2$ can combine with the carbon to which they are attached to complete a carbocyclic ring such as cyclopropyl, cyclobutyl, cyclohexyl, and cyclopentyl. Similarly, $R_3$ and $R_4$ can be taken together with the carbon to which they are attached to complete a $C_3$–$C_6$ carboxylic ring such as cyclopropyl, cyclohexyl, and the like.

$Y_1$ and $Y_2$ in Formula I independently include the group $COOR_5$ where $R_5$ is alkyl, alkenyl, or alkynyl, or substituted alkyl, alkenyl, or alkynyl. These groups are illustrated above for $R_1$, $R_2$, $R_3$, and $R_4$.

The compounds of the invention which have at least one carboxylic acid group (i.e., one of $Y_1$ and $Y_2$ is COOH) readily form pharmaceutically acceptable salts by reaction with organic or inorganic bases. Typical bases commonly utilized to form salts include sodium hydroxide, potassium hydroxide, sodium carbonate, triethyl amine, pyridine, ammonia, and the like.

Typical compounds provided by the invention are depicted below:

| n | m | $R_1$ | $R_2$ | $R_3$ | $R_4$ | $Y_1$ | $Y_2$ |
|---|---|---|---|---|---|---|---|
| 2 | 3 | $CH_3$ | $CH_3$ | $CH_3$ | $CH_3$ | COOH | COOH |
| 3 | 3 | $CH_3$ | $CH_3$ | Et | Et | $COOCH_3$ | COOH |
| 2 | 4 | Et | i-Pr | Et | Et | COOH | $COOCH_3$ |
| 3 | 4 | 3-chloropropyl | $CH_3$ | $CH_3$ | 2-hydroxyethyl | COOH | CHO |
| 4 | 4 | $CH_3$ | $CH_3$ | $CH_3$ | $CH_3$ | COOH | COOH |
| 4 | 4 | Et | Et | Et | Et | $COO^-Na^+$ | $COO^-Na+$ |
| 4 | 4 | Et | $CH_3$ | n-Bu | n-Bu | COOH | $COOCH_3$ |
| 4 | 4 | $HOCH_2$ | $HOCH_2$ | $HOCH_2$ | $HOCH_2$ | COOEt | COOEt |
| 4 | 4 | nPr | nPr | nPr | nPr | tetrazolyl | CHO |
| 4 | 4 | △ | | △ | | COOH | COOH |
| 4 | 4 | ⬠ | | $CH_3$ | $CH_3$ | CHO | CHO |
| 4 | 4 | phenylmethyl | $CH_3$ | $CH_3$ | $CH_3$ | CHO | CHO |
| 4 | 5 | $CH_3$ | $CH_3$ | Et | Et | COOH | CHO |
| 4 | 5 | Et | iPr | iPr | Et | COOH | COOH |
| 2 | 5 | n-hexyl | n-hexyl | n-hexyl | n-hexyl | COOH | COOH |
| 2 | 6 | iBu | iBu | nPr | nPr | $COO^-K^+$ | $COO^-K^+$ |
| 3 | 6 | $CH_3$ | $CH_3$ | Et | Et | COOH | COOH |
| 3 | 7 | $HOCH_2$ | $ClCH_2$ | $BrCH_2$ | $ICH_2$ | COOH | COOH |
| 4 | 7 | n-pentyl | n-pentyl | $CH_3OCH_2-$ | $CH_3OCH_2-$ | $COO^-Et_3N^+$ | COOH |
| 4 | 8 | $CH_3$ | $CH_3$ | $CH_3$ | $CH_3$ | CHO | COOH |
| 4 | 9 | $CH_3$ | $CH_3$ | $CH_3$ | $CH_3$ | COOn-hexyl | COOEt |
| 5 | 8 | Et | Et | Et | Et | tetrazolyl | tetrazolyl |
| 9 | 9 | Et | Et | $ClCH_2$ | phenylmethyl | COOH | COOH |

The compounds of this invention are prepared utilizing methodology well known in the field of organic chemistry. In a typical synthesis, a carboxy substituted alkyl halide is reacted with a carboxy substituted alkanol in the presence of a base to effect a condensation to provide the invention compound. Carboxy esters typical are utilized, thereby providing invention compounds where $Y_1$ and $Y_2$ both are $COOR_5$. Simple saponification converts one or both of the ester groups to the free acid when desired. The foregoing condensation reaction is depicted as follows:

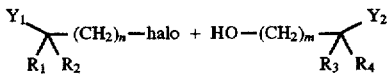

where halo is bromo, chloro, iodo, or the like, and $Y_1$ and $Y_2$ are preferably $COOR_5$, although the reaction works equally well when $Y_1$ and $Y_2$ independently are tetrazolyl or CHO. The reaction generally is carried out by first reacting the alkanol with about an equimolar quantity of a base such as sodium hydride or metallic sodium, generally in an unreactive organic solvent such as benzene, toluene, xylene, tetrahydrofuran, or the like. This produces the oxide form of the alkanol, which then readily reacts with an equimolar quantity of an alkyl halide to produce an invention compound. The reaction generally is substantially complete within about 2 to about 10 hours when carried out at an elevated temperature of about 50° C. to about 120° C. The invention compound is readily isolated by simply removing the reaction solvent, for instance by evaporation. The product can be purified if needed by common methods such as crystallization from solvents such as ethyl acetate, benzene, hexane, and the like, or chromatography, for example, over solid supports such as silica gel.

An alternative method for preparing the invention compounds entails reaction of a halo substituted dialkyl ether with an α,α-disubstituted acetic acid or ester, ethanal, or a methyltetrazole. Such reaction is depicted as follows:

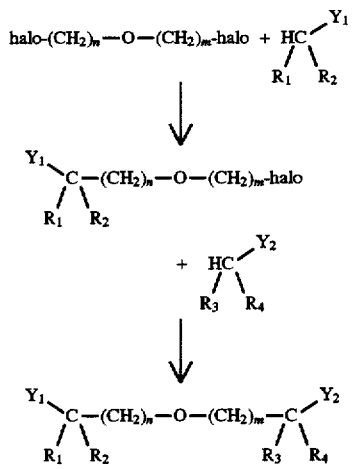

The above process is preferably utilized for preparing invention compounds wherein $R_1$ and $R_2$ are the same as $R_3$ and $R_4$, respectively, and where $Y_1$ and $Y_2$ are the same. In such case, the halo substituted dialkyl ether is reacted with 2 equivalents, or more, of the acetic acid derivative or tetrazole, for example, a compound such as

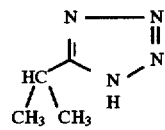

The reaction generally is carried out in a mutual solvent such as tetrahydrofuran, dioxane, diethyl ether, or the like, and in the presence of a base such as sodium hydride, metallic sodium, butyl lithium, or the like. The reaction generally is complete within about 2 to about 10 hours when conducted at a temperature of about 0° C. to about 50° C. The product, a compound of the invention, is readily isolated by removing the reaction solvent, and further purification can be accomplished by routine methods if desired, including chromatography, crystallization, and the like.

It may be desirable at times to protect some reactive groups with removable organic radicals so as to prevent unwanted side reactions. For example, hydroxy and free carboxy groups can be derivatized with radicals which eliminate their ability to enter into chemical reactions that are carried out, and wherein the radical can be easily removed when desired to regenerate the free hydroxy or carboxy group. Typical hydroxy and carboxy protecting groups, and methods for their attachment and subsequent removal, are fully discussed by Greene and Wirts in "Protective Groups in Organic Synthesis", 2nd Ed., John Wiley & Sons, Inc., New York, N.Y., 1991. For example, hydroxy groups are readily protected by conversion to o-benzyl group, which are easily cleaved when desired by hydrogenolysis. Carboxy groups generally are converted to esters, for example, para-nitrobenzyl esters or 2,2,2-trichloroethyl esters. Such ester groups are readily hydrolyzed when desired to afford the free carboxy group.

As noted above, the carboxylic acids of this invention readily form salts by reaction with an inorganic base or organic base. Preferred salts include inorganic salts made with bases such as sodium hydroxide, potassium hydroxide, calcium hydroxide, and the like. Typical organic bases include triethylamine, pyridine, methylamine, and the like.

The following detailed examples further illustrate the synthesis of compounds of this invention. The examples are illustrative only and are not to be construed as limiting in any respect.

EXAMPLE 1

6,6'-Oxybis(2,2-dimethylhexanoic acid)

To a stirred solution of sodium hydride (28 g of 60% dispersed in mineral oil, 700 mmol) in 600 mL of dry tetrahydrofuran containing 61 g (600 mmol) of diisopropylamine were added 52.9 g (600 mmol) of isobutyric acid. The reaction mixture was stirred at 24° C. for 30 minutes, and then cooled to 0° C. in an ice/acetone bath. To the cold solution were added 286 mL of a 2.1M solution of n-butyl lithium (600 mmol), and the mixture was stirred at 0° C. for 1 hour. To the cold stirred reaction mixture were added 59.7 g (297 mmol) of 4,4'-dichlorobutyl ether dropwise over 15 minutes. The mixture was warmed to 24° C. and stirred for 48 hours. The reaction mixture was diluted by addition of 600 mL of water. The aqueous layer was separated, washed with 200 mL of diethyl ether, and then acidified to pH 5.0 (Congo red) with about 150 mL of 6N hydrochloric acid. The aqueous acid solution was extracted three times with 300 mL portions of diethyl ether. The ethereal extracts were combined, washed with brine, dried over $MgSO_4$, and the solvent was removed by evaporation under reduced pressure to provide the product as an oil. The oil was distilled at 160°

C. at 3 mm Hg to provide 66.7 g of 6,6'-oxybis(2,2-dimethylhexanoic acid), mp 49°–51° C.

Analysis calcd. for $C_{16}H_{30}O_5$: C, 63.47; H, 9.88. Found: C, 63.75; H, 10.00.

EXAMPLES 2 THROUGH 9

By following the general procedure of Example 1, the following compounds were prepared:

7,7'-oxybis(2,2-dimethylheptanoic acid), 5,5'-oxybis(2,2-dimethylpentanoic acid), 4,4'-oxybis(2,2-dimethylbutanoic acid), 8,8'-oxybis(2,2-dimethyloctanoic acid), Ethyl 2,2-dimethyl-5-(4-methyl-4-ethoxycarbonyl pentyloxy)pentanoate, Ethyl 2,2-dimethyl-6-(5-methyl-5-ethoxycarbonyl hexyloxy)hexanoate, Methyl 2,2-dimethyl-8-(7-methyl-7-methoxycarbonyl octyloxy)octanoate, and 7-(4-Methyl-4-hydroxycarbonylpentyloxy)-2,2- dimethylheptanoic acid.

As noted above, the dialkyl ethers of this invention are useful for treating and preventing vascular disease such as coronary heart disease, stroke, restenosis, and the like, by virtue of their ability to lower plasma cholesterol levels of triglyceride-rich lipoprotein such as LDL, and raise cholesterol levels of HDL. The compounds are particularly effective at lowering Lp(a), as well as elevating HDL-cholesterol.

Figure 1:
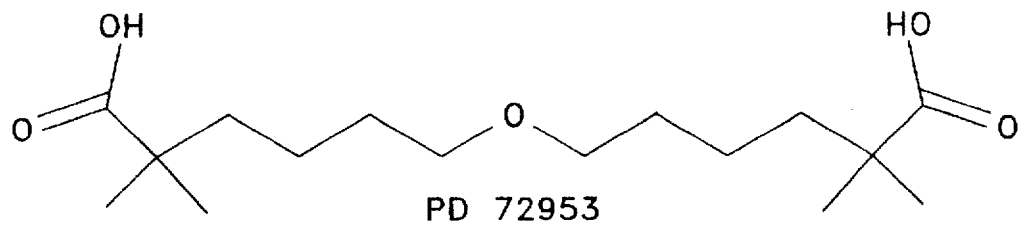
FIG. 1 shows the structure of the preferred compound of Example 1, which is also identified as PD 72953.
Figure 2A:
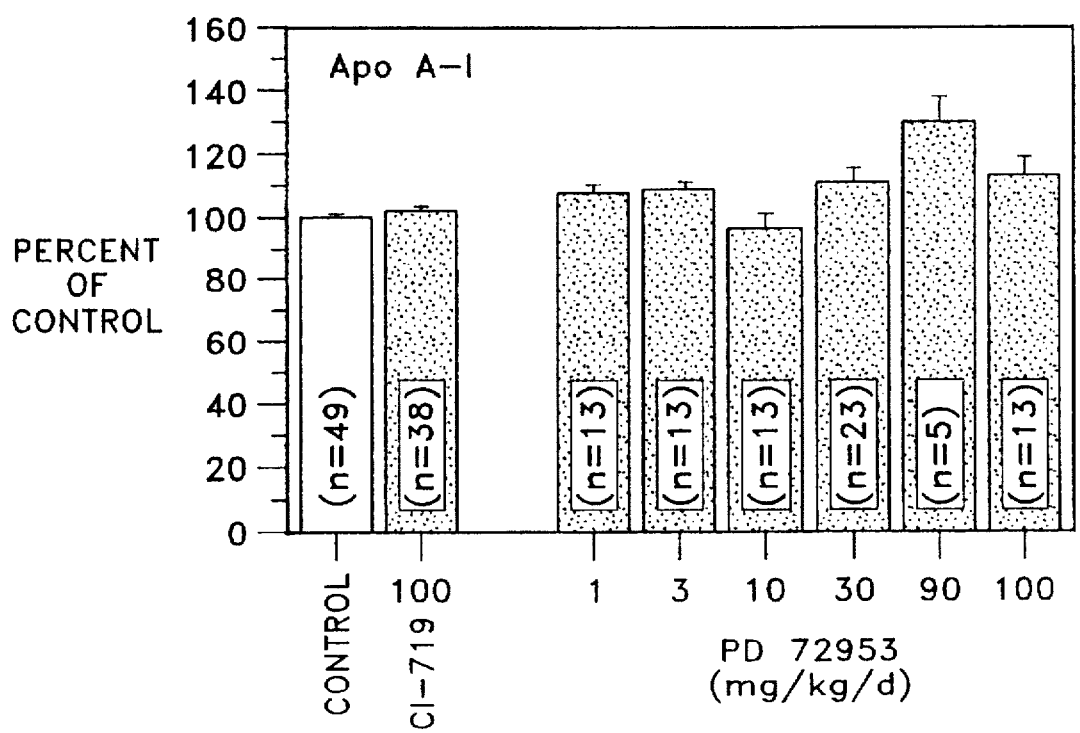
FIG. 2 shows the dose-response on various lipoprotein, cholesterol, and triglyceride levels in rats caused by PD 72953, along with the effects caused by the commercial standard gemfibrozil (CI-719).
Figure 2B:
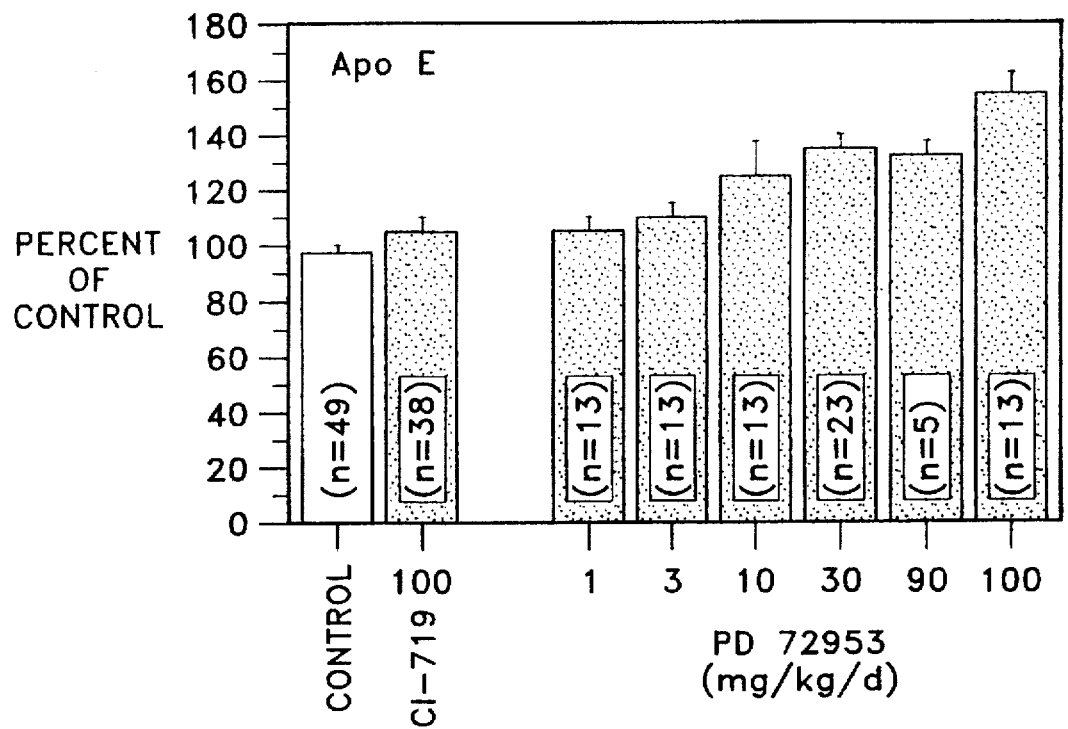
Figure 2C:
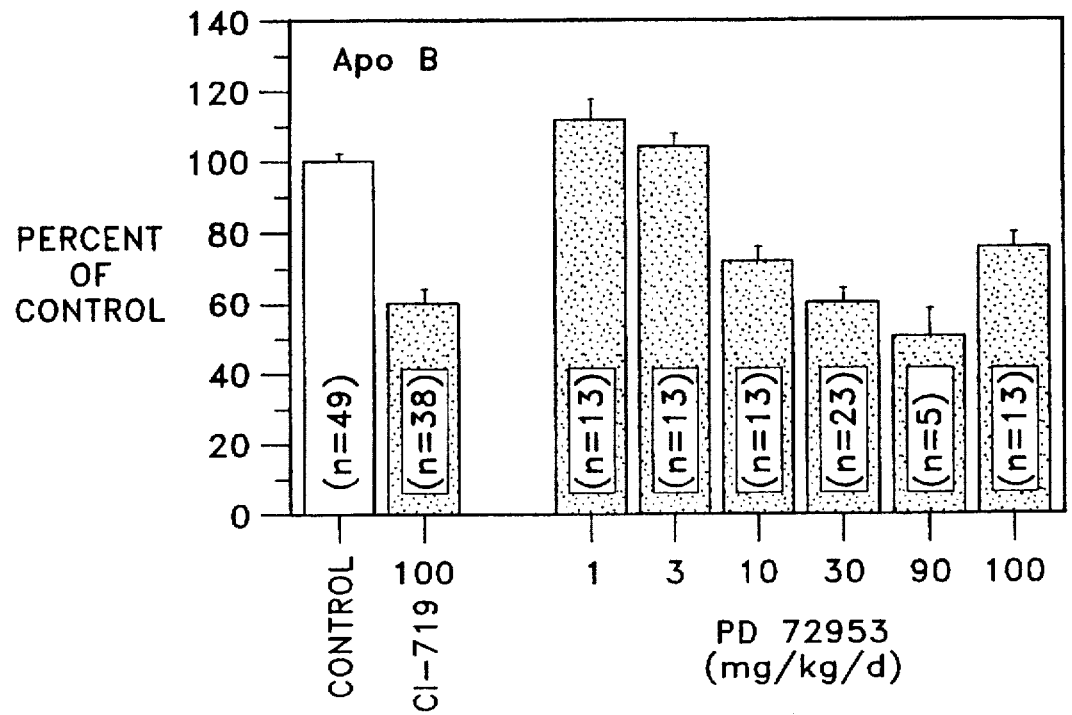
Figure 2D:
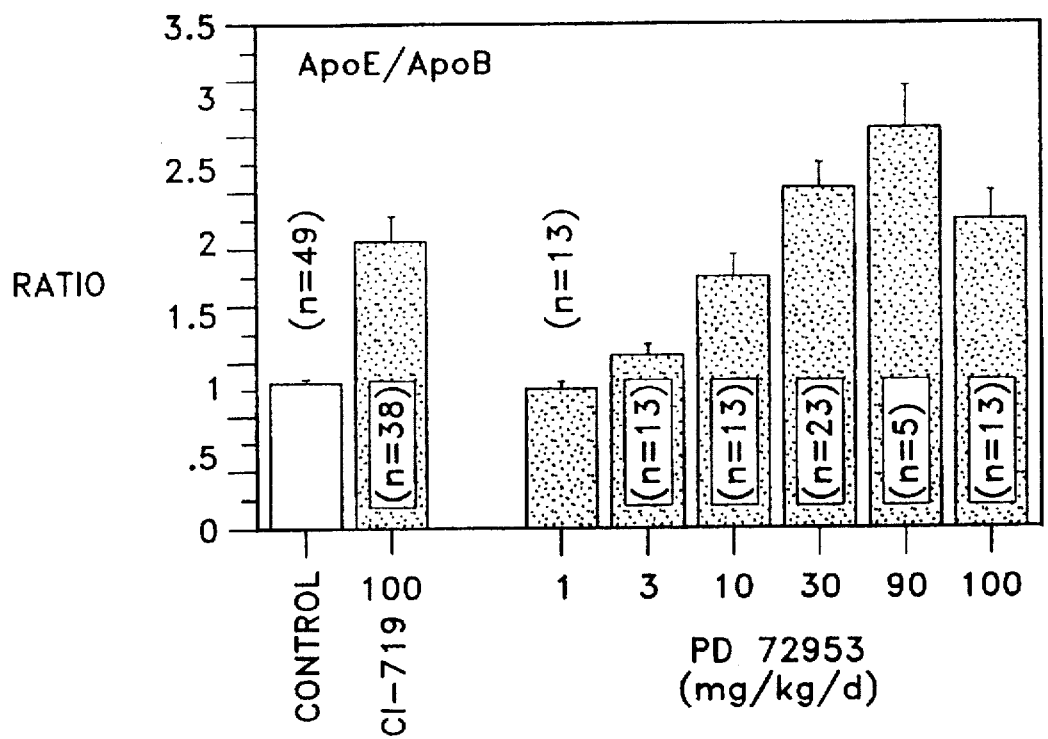
Figure 2E:
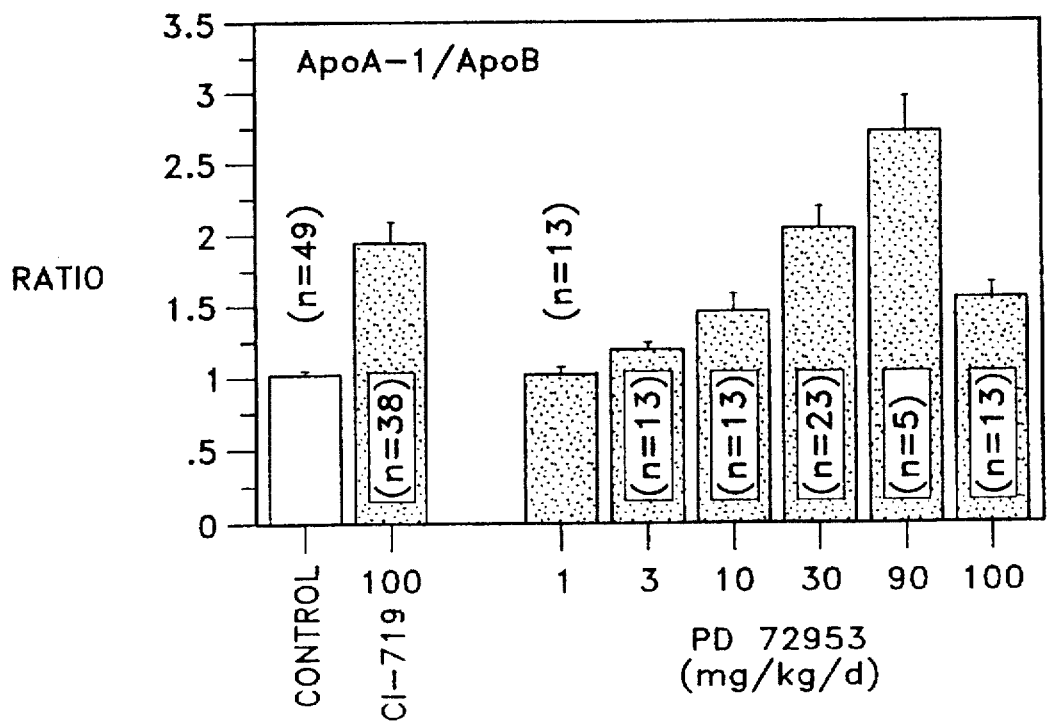
Figure 2F:
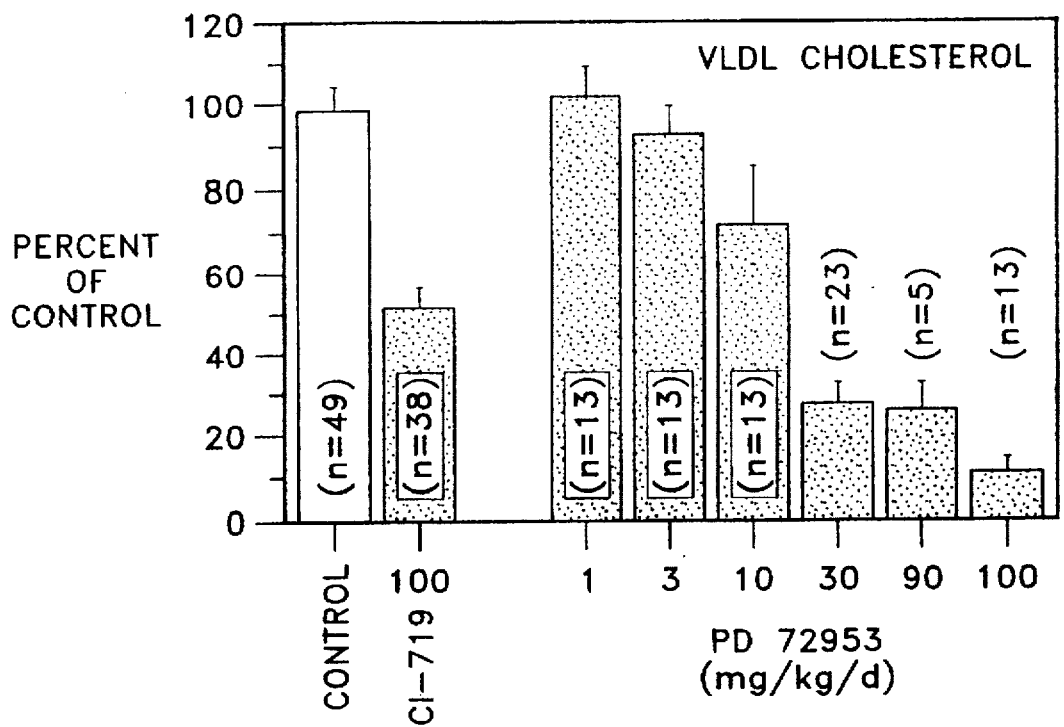
Figure 2G:
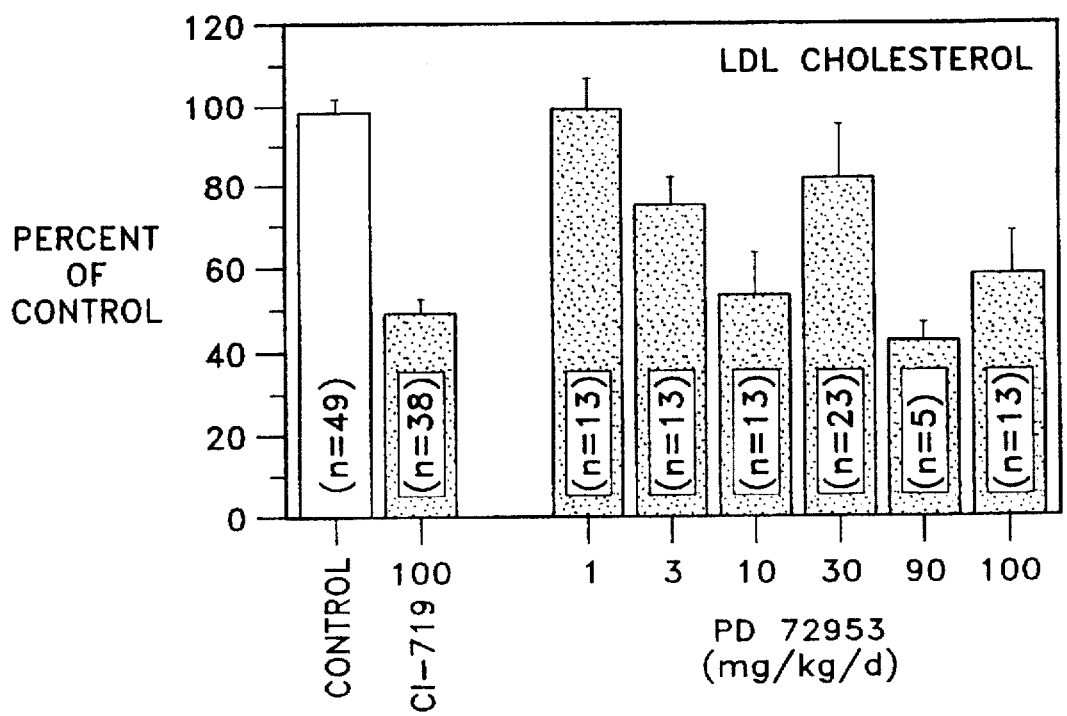
Figure 2H:
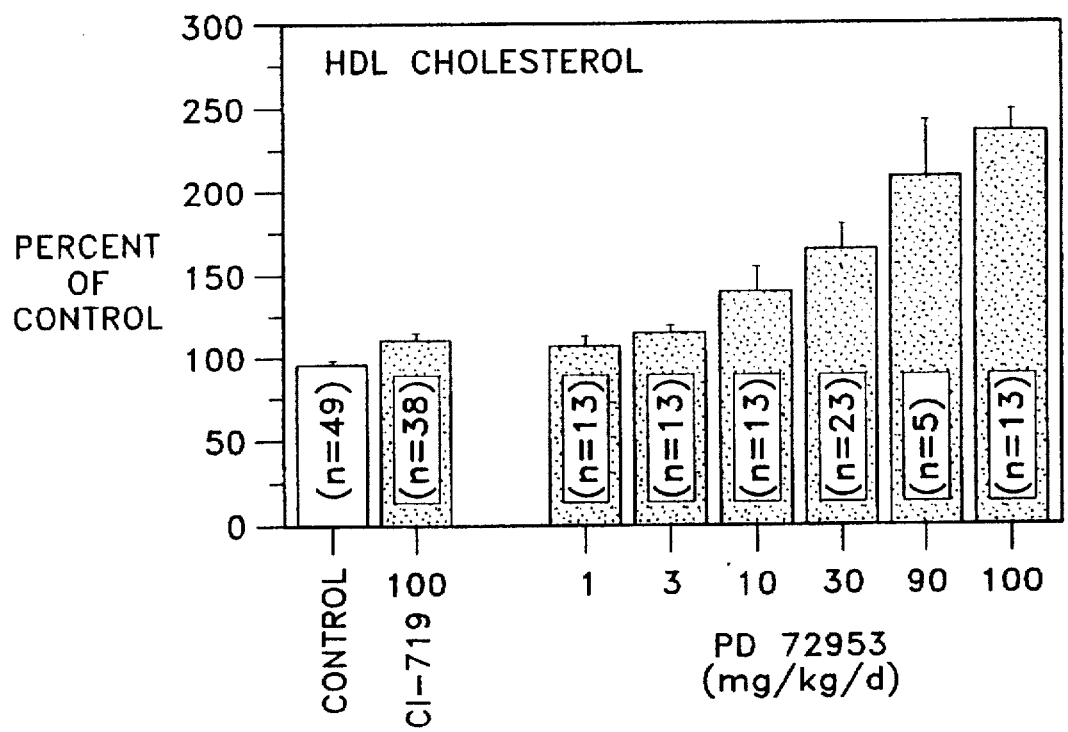
Figure 2I:
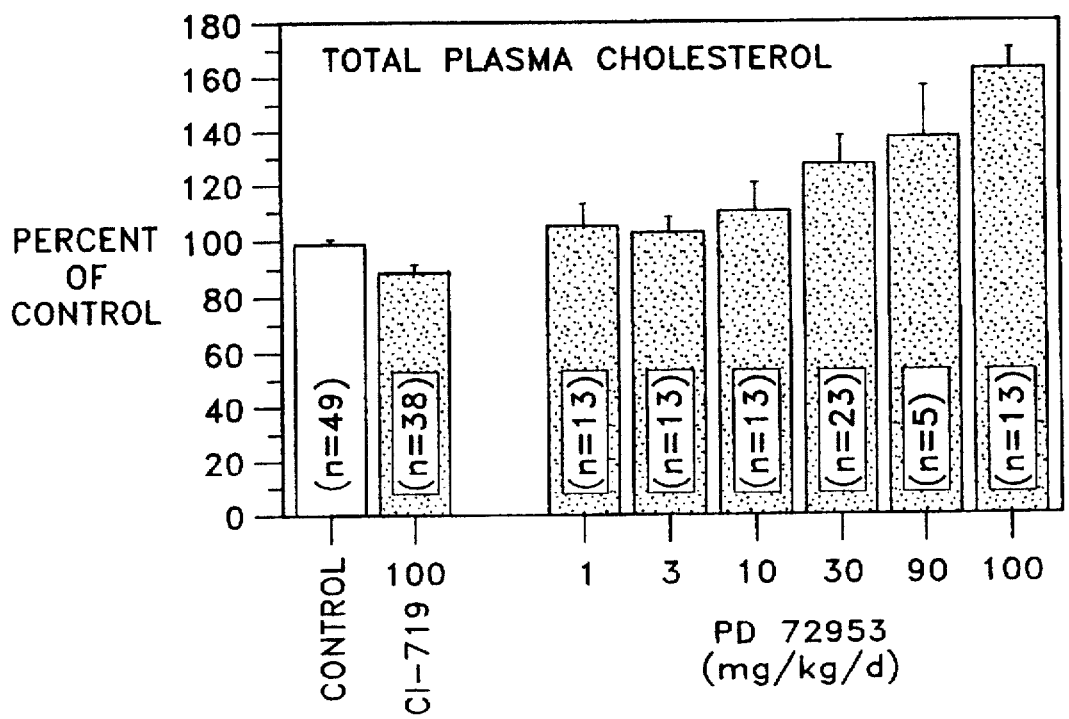
Figure 2J:
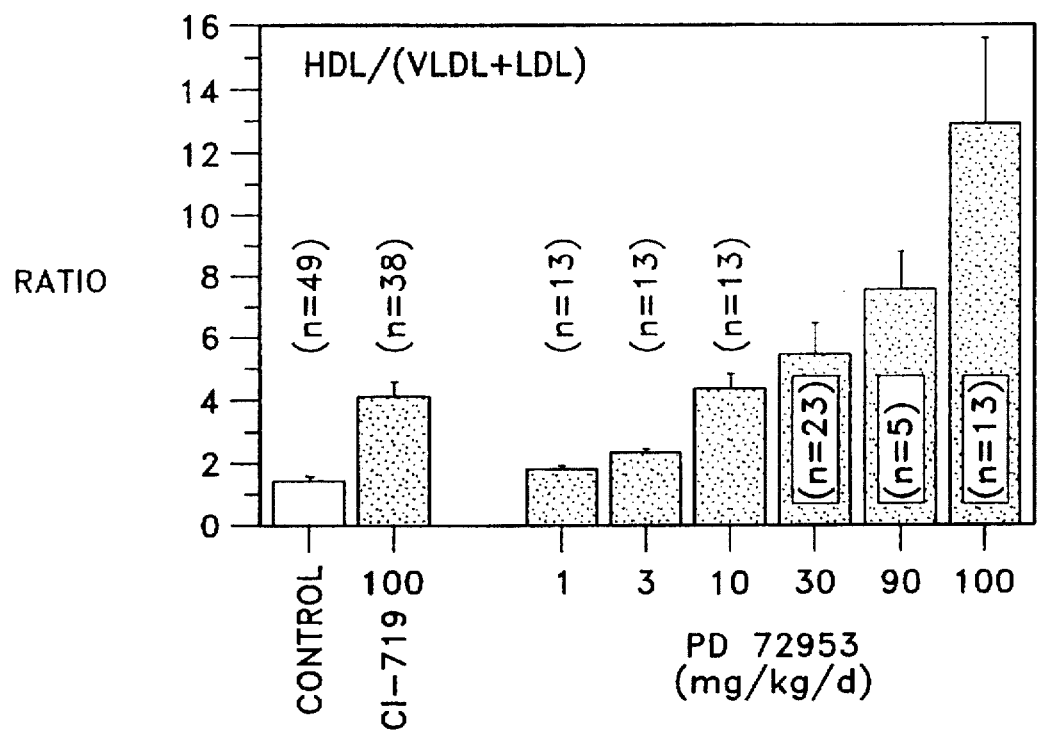
Figure 2K:
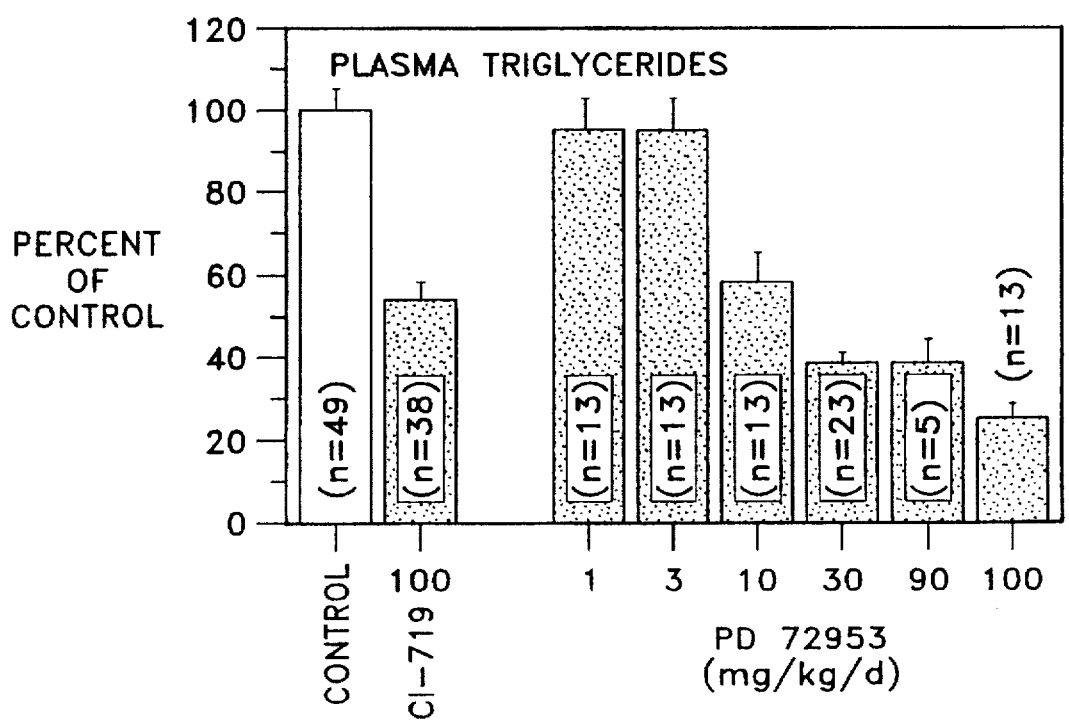
Figure 2L:
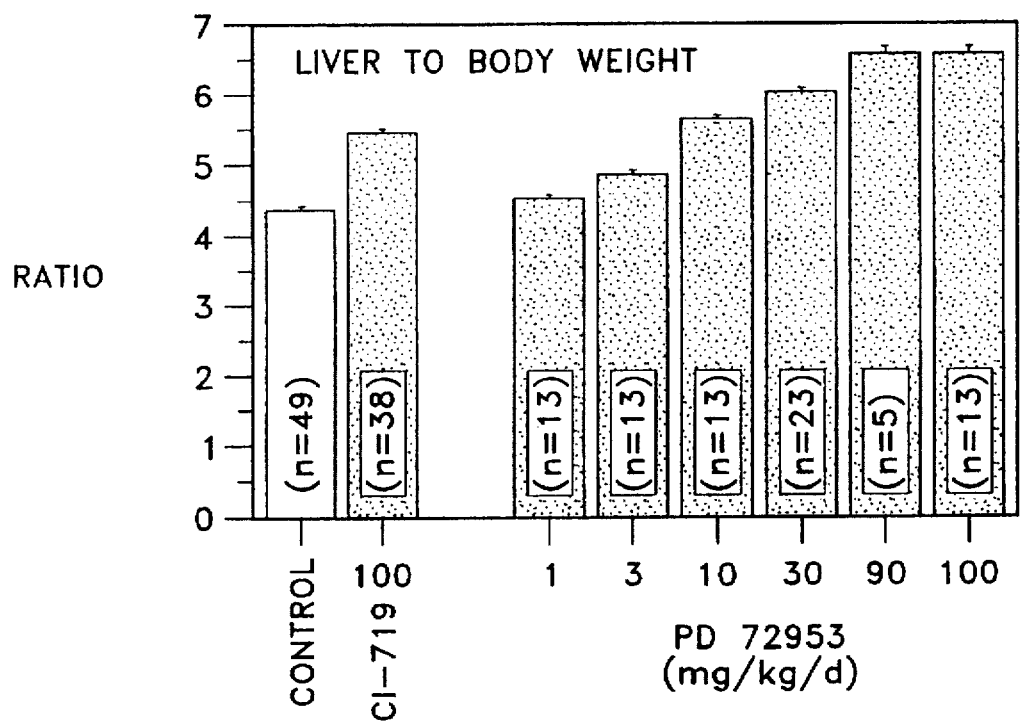
Figure 2M:
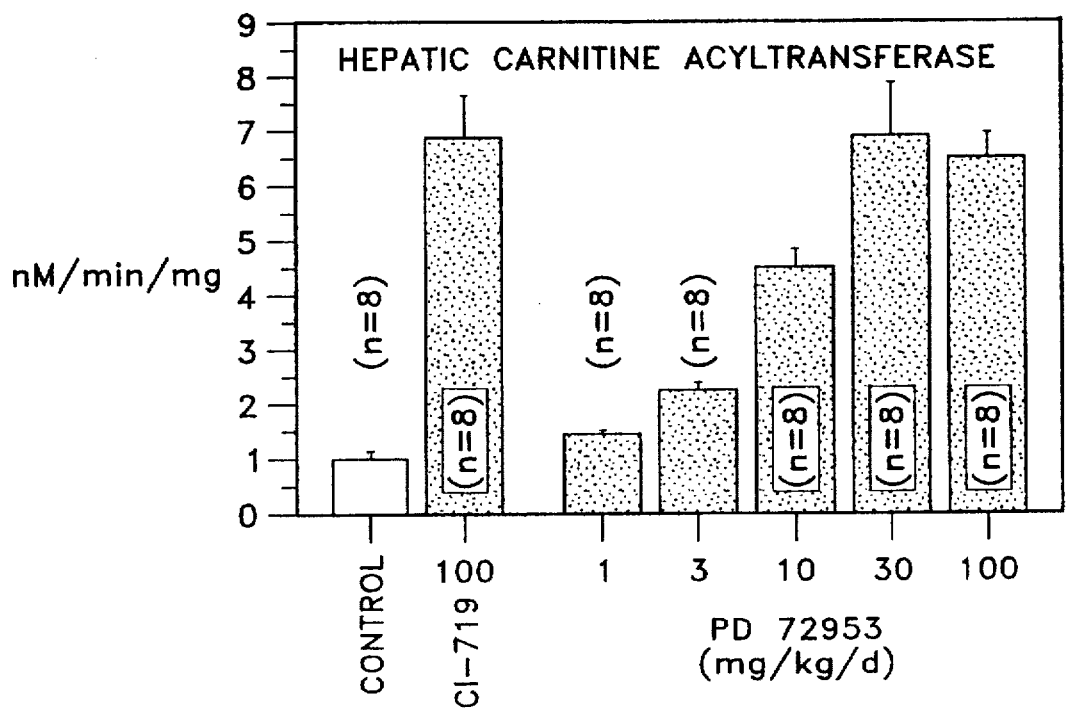

The ability of the dialkylether derivatives of Formula I to lower Lp(a) and elevate HDL-cholesterol was determined in in vivo studies routinely utilized by those skilled in the art. Animal studies in rats were conducted according to the following protocol.

Male Sprague-Dawley rats (100–200 g) were obtained from Charles River Laboratories and housed 3 to 6 rats per cage and allowed Purina rat chow and water ad libitum in temperature controlled rooms, under a 12-hour light/dark cycle beginning with lights on at 6 AM. Rats were dosed daily between 6 to 9 AM by oral gavage with test compounds dissolved or suspended in a 0.2% Tween-20 plus 1.5% carboxymethylcellulose (in water) vehicle or with vehicle alone. Vehicle volume represented 0.25% of body weight and gemfibrozil (100 mg/kg/d) was used as a reference agent for all studies. Test compounds were administered up to 100 mg/kg/d for 7 to 14 days. Rats in the nonfasted state were euthanized by ether inhalation, weighed, bled from the heart, and subjected to hepaticotomy for liver weight determinations. Blood was transferred to EDTA containing vacutainer tubes for plasma isolation. Cynomolgus monkey blood was drawn directly into vacutainer tubes for isolation of serum and plasma.

Male cynomolgus monkeys (*Macaca fascicularis*) were obtained from Charles River Laboratories (Wilmington, Mass.) and individually housed and fed a daily diet consisting of 20 normal monkey chow biscuits (Ralston Purina, St. Louis, Mo.) and fruit (1 banana and 12 grapes). The monkeys were pre-trained in basic primate restrainers (Primate Products, Woodside, Calif.) and were also equipped with vascular access ports (Norfolk Medical Products, Skokie, Ill.) for obtaining blood samples. The effects of the compound of Example 1 were studied in a rising-dose fashion. Over a 3-week period, three pre-study basal blood samples were obtained from the chair-restrained monkeys from the vascular ports. For studies with Example 1, monkeys were restrained in chairs and orally dosed daily by gavage with 3 mg/kg (Week 1), 10 mg/kg (Week 2), and 30 mg/kg (Week 3) of the Example 1 compound suspended in a 0.2% Tween-20 plus 1.5% carboxymethylcellulose vehicle between 5 to 7 AM. During the study period, weekly bloods were drawn 24 hours post-dosing from fasted animals. Additional blood samples from fasted monkeys were obtained 1 week after treatment with Example 1 ceased. Food consumption and observed behavior was normal throughout the study.

Monkey plasma samples were kept on ice, aliquoted to multiple microfuge tubes, and promptly frozen and stored at –70° C. Serum samples were stored at 4° C. prior to analysis for specific serum enzymes or albumin as described below.

Sample Analysis

Triglycerides were determined using a commercially available kit (Trigli-cinct2, Sclavo, Siena, Italy, or Triglyceride G, Wako Pure Chemical Industries, Ltd; Osaka, Japan). Total plasma cholesterols were determined enzymatically as described by Allain, et al., *Clin. Chem.*, 20:470–474 (1974). Plasma total cholesterol lipoprotein profiles were determined by on-line post-column analysis on Superose 6 high performance gel chromatography (HPGC) on a Rainin HPLC (see Kieft, et al., *J. Lipid Res.*, 32:859–866 (1991)). Lipoprotein cholesterol was determined from total cholesterol determination and percent area distribution of cholesterol determined by HPGC.

Apolipoprotein A-I and E in whole plasma were quantitated by rocket immunoelectrophoresis by the method of Laurell, et al., *Methods Enzymol*, 73:339–369 (1981) using antibodies raised in a rabbit against rat apo A-I, in a goat against rat apo E (from Dr Patrick Tso, LSU Medical Center, Shreveport, La.). Plasma samples were diluted in 4M urea, 1% Triton X-100, 12 mM Tricine, 40 mM Tris, 0.6 mM calcium lactate, 0.01% sodium azide, pH 8.2, and incubated for 60 minutes at 52° C. prior to immunoelectrophoresis. Appropriate dilutions of rat plasma were made to determine apolipoproteins were in the linear range of the assay. Immunoelectrophoresis was carried out on GelBond film (Cat 53748, FMC Bioproducts, Rockland, Me.) usually containing either 4% rabbit anti-rat apo A-I or 2% goat anti-rat apo E antiserum in 1% agarose, 2% polyethylene glycol 6000 in 24 mM Tricine, 80 mM Tris, and 1.2 mM calcium lactate. Rocket height was determined on amido black-stained gels. For data analysis, apolipoproteins in plasma from animals in the control groups was arbitrarily set to 100.

Rat apo B was assessed in microtiter plates with minor modifications described by Rifai, et al., *Clin. Chem.*, 32:957–961 (1986), i.e., an immunoturbidometric method utilizing antibodies to mouse apo B raised in sheep that cross-reacts with rat apo B. Plasma samples from experimental animals (5, 10, 20, and 30 µL) or a pooled rat plasma standard (0–50 µL) were combined with 2M urea, 10% sheep anti-mouse apo B serum, 1.6% polyethylene glycol 8000 (final concentrations) in a total volume of 200 µL of phosphate-buffered saline. Turbidity (OD=340 nm) was determined initially and following an overnight incubation at room temperature utilizing a Titertek Multiscan MCC/ 340MK II (Flow Laboratories) 96-well absorbance spectrophotometer. An appropriate dilution of rat plasma (usually 10 µL) was utilized to determine apo B in the linear range of the assay. For data analysis, apo B levels in the plasma of drug-treated animals was compared to that obtained in the control group which was arbitrarily set to 100 for each experiment.

Lp(a) levels in monkeys were assayed with a commercially available Lp(a) ELISA kit (Apo-Tek Lp(a) Elisa Test System, Organon Teknika, Biotechnology Research Institute) developed for the detection of human Lp(a). Lp(a) is quantitated by a sandwich technique in which apo(a) is captured by anti-apo(a) (coated microtiter plates) is determined by its association with apo B by a soluble, enzymatically linked antibody. Standard curves generated with human and cynomolgus monkey plasma were parallel suggesting this assay could be used to quantitate cynomolgus monkey Lp(a). Lp(a) measurements for all cynomolgus monkey plasmas were determined in a single assay carried out in triplicate for samples thawed only once.

In chow-fed rats, gemfibrozil was compared to the Example 1 compound for its potential to affect a variety of lipid parameters. These data represent pooled data from several separate 1-week studies and a single 2-week study (N=8 rats/group). Data for each study were normalized to values obtained with the vehicle-treated rats from each study. Gemfibrozil (100 mg/kg/d) had no effect on plasma apo A-I which increased mostly at the higher doses of Example 1 compound. Apo E was only slightly elevated with gemfibrozil, but markedly elevated dose dependently with Example 1. These data are largely weighted to 1-week studies (1 week, N=30; 2 week, N=8) and therefore do not reflect the marked elevation of plasma apo E observed with gemfibrozil at 2 weeks. Both gemfibrozil and the compound of Example 1 significantly reduced apo B. These apolipoprotein changes can also be appreciated as ratios of either apo E to apo B or apo A-I to apo B. Plasma lipid parameters including total cholesterol, lipoprotein cholesterol, and triglycerides are also favorably affected by the compound of Example 1 (FIG. 2). Total plasma cholesterol was slightly diminished by 100 mg/kg gemfibrozil but elevated in a dose-dependent fashion by the compound of Example 1. This effect was mainly reflected in elevation of HDL-cholesterol. Both gemfibrozil and Example 1 reduced VLDL- and LDL-cholesterol. These effects can be appreciated as the ratio of HDL-cholesterol to VLDL- plus LDL-cholesterol, whereby 100 mg gemfibrozil elevated this ratio to a similar level to that of 10 mg of Example 1 (1- to 2-fold), while higher levels (30–100 mg) of Example 1 further increased this ratio reaching an 8- to 9-fold elevation at the highest concentration tested. Both gemfibrozil and the compound of Example 1 reduced plasma triglycerides.

Figure 3:
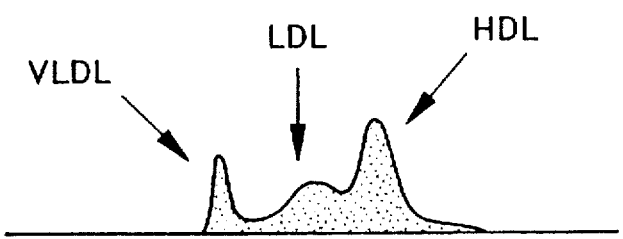
FIG. 3 shows the effect of various doses of PD 72953 on total cholesterol in rats, and establishes that at 100 mg/kg, PD 72953 essentially eliminates VLDL and LDL, and increases HDL, even to a greater extent than the same dose of gemfibrozil.
Figure 3A:
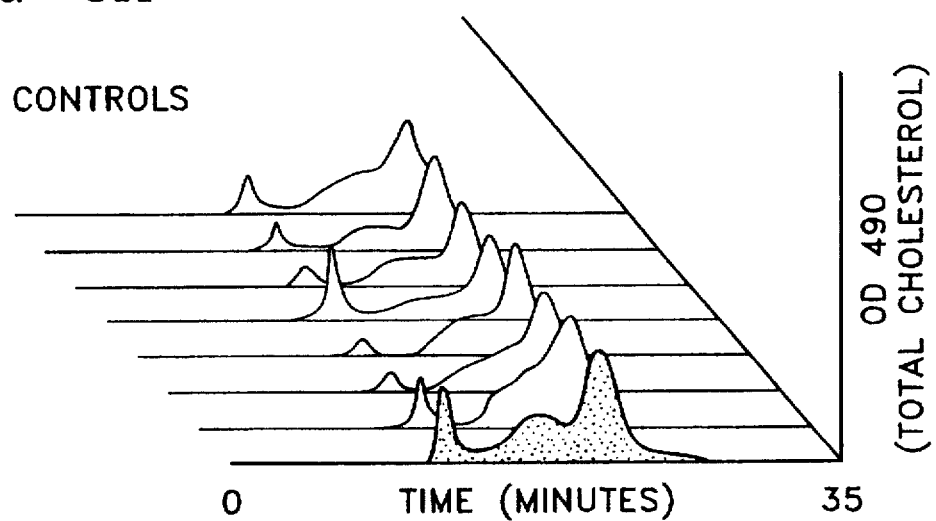
Figure 3B:
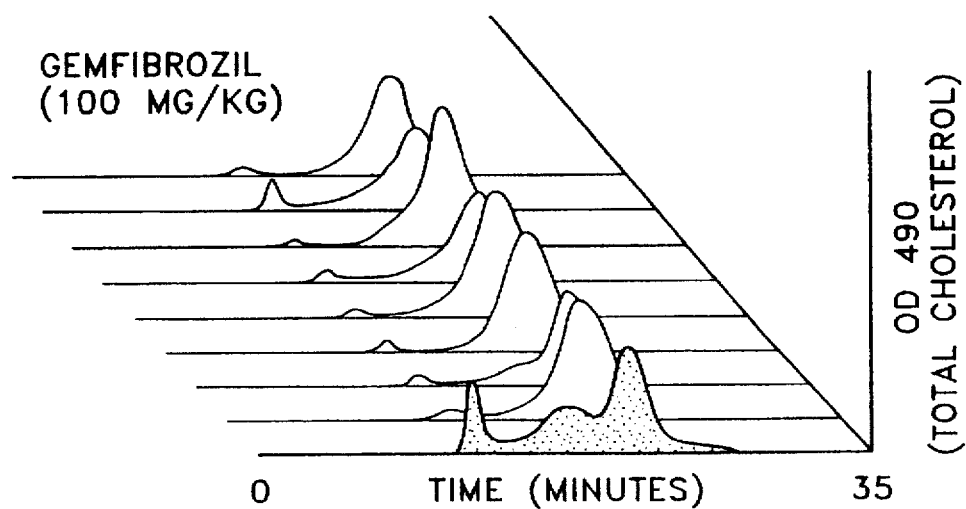
Figure 3C:
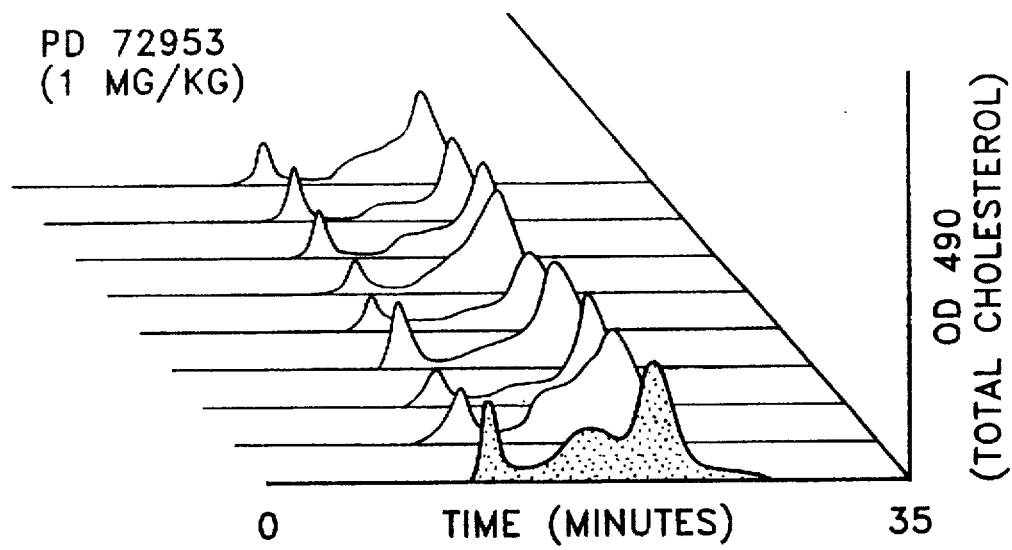
Figure 3D:
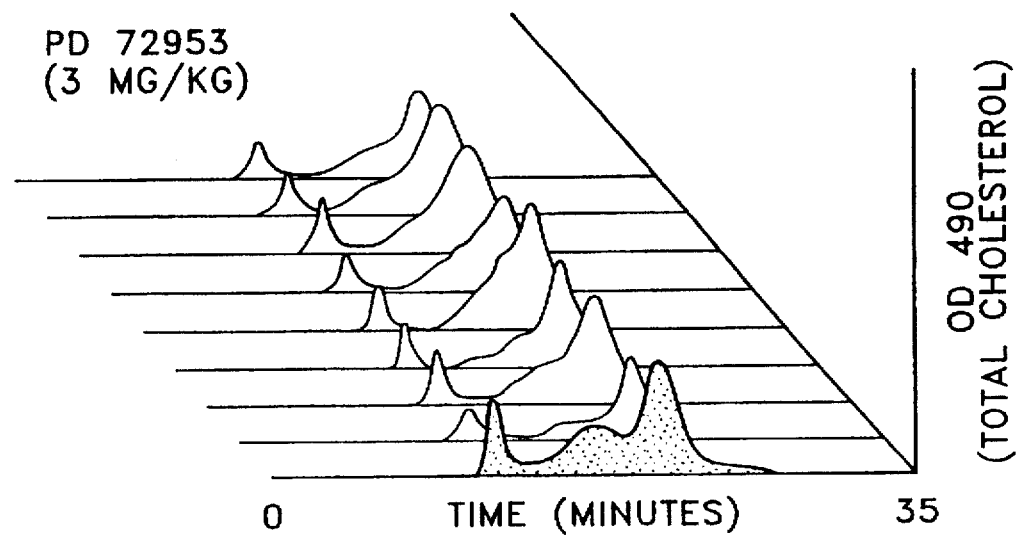
Figure 3E:
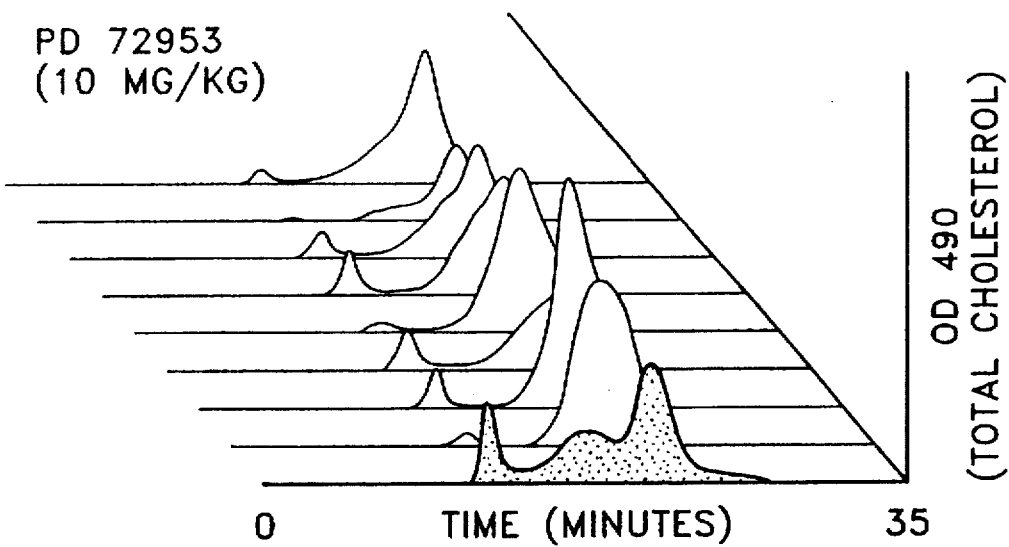
Figure 3F:
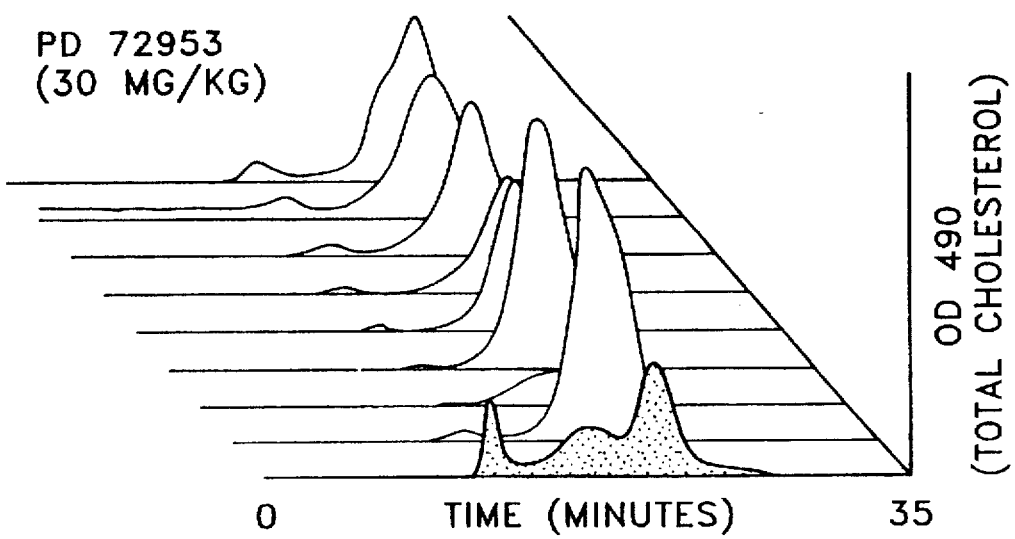
Figure 3G:
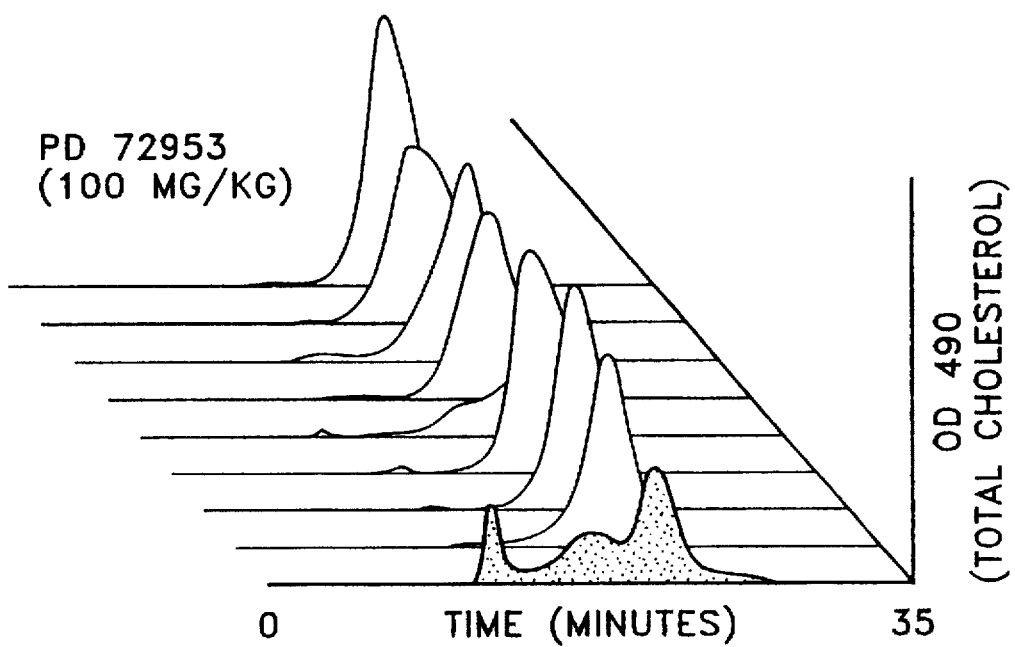
Figure 4:
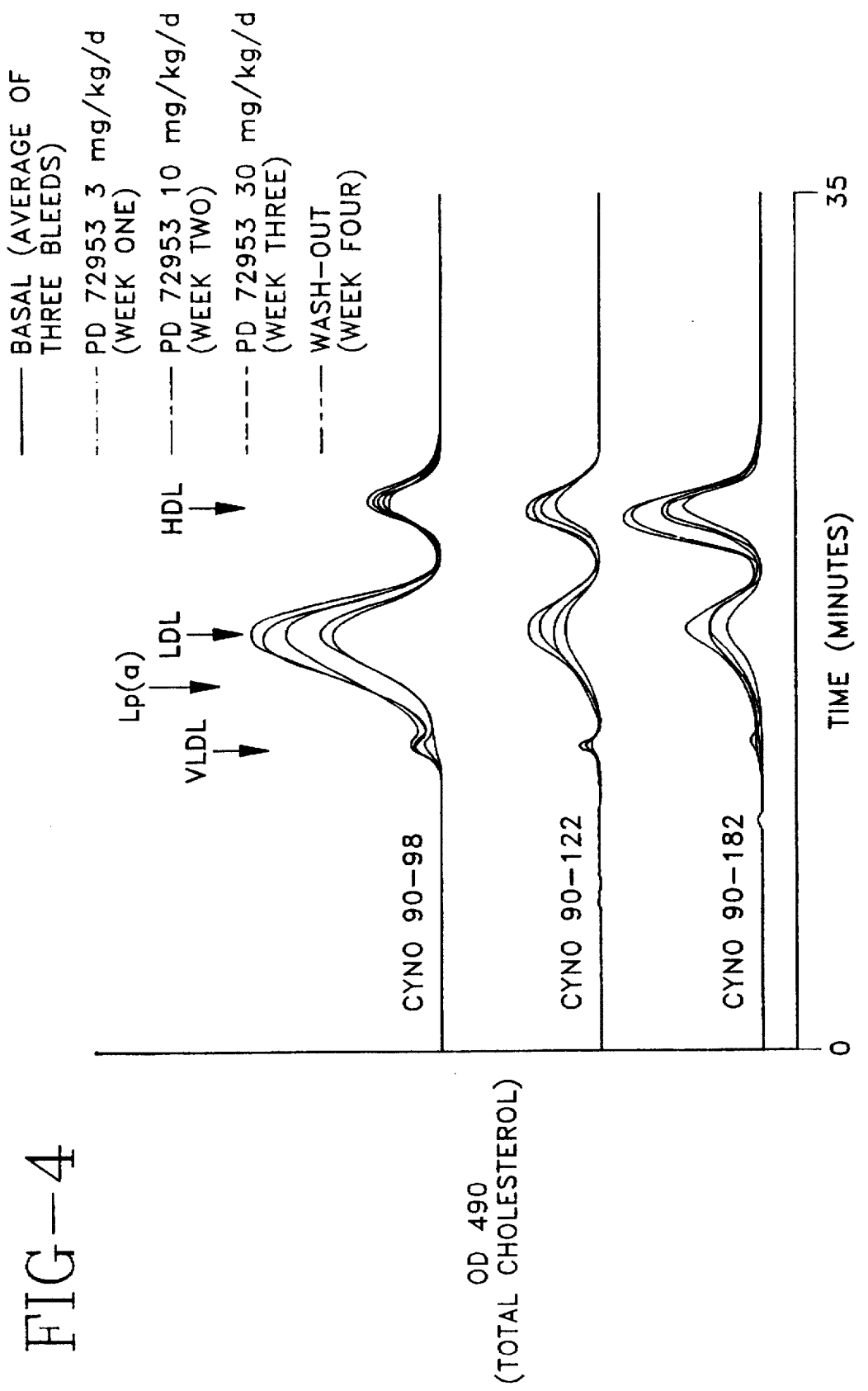
FIG. 4 shows the effect of various doses of PD 72953 on total cholesterol in monkeys, and establishes that continued dosing causes continued drop in cholesterol.

High performance gel chromatography (HPGC) was used to characterize lipoprotein cholesterol profiles in rats (FIG. 3) and cynomolgus monkeys treated with the compound of Example 1 (FIG. 4). FIG. 3 is lipoprotein cholesterol profiles from rats (8/group) treated with vehicle alone, 100 mg/kg/d gemfibrozil or 1, 3, 10, 30, or 100 mg/kg/d of the compound of Example 1 for 2 weeks. Each profile is from a single rat. All profiles are drawn to the same scale, and the profile of the first rat in the control group (darkened profile) is overlaid in front of each treatment group for comparison. Profiles of the gemfibrozil group at 100 mg/kg/d were similar to those of the Example 1 compound at 3 to 10 mg/kg/d. At treatment doses of Example 1, the effects on lipoprotein cholesterol are exaggerated further, including attenuation of VLDL- and LDL-cholesterol and elevation of HDL-cholesterol.

HPGC was also used to characterize lipoprotein cholesterol profiles in three male cynomolgus monkeys prior to, during, and following treatment with the compound of Example 1. The animals were pre-selected to represent animals with either high, average, or low LDL- to HDL-cholesterol ratios. The three basal profiles from each monkey were essentially identical and therefore pooled and averaged to generate a representative basal profile. One-week treatment with 3 mg/kg/d of the Example 1 compound did not affect lipoprotein cholesterol profiles. However, treatment with 10 mg/kg/d of Example 1 during Week 2, and 30 mg/kg/d during Week 3, progressively decreased VLDL-, LDL-, and HDL-cholesterol, which began to rebound to control levels in two of three monkeys after a 1-week washout period.

Figure 5A:
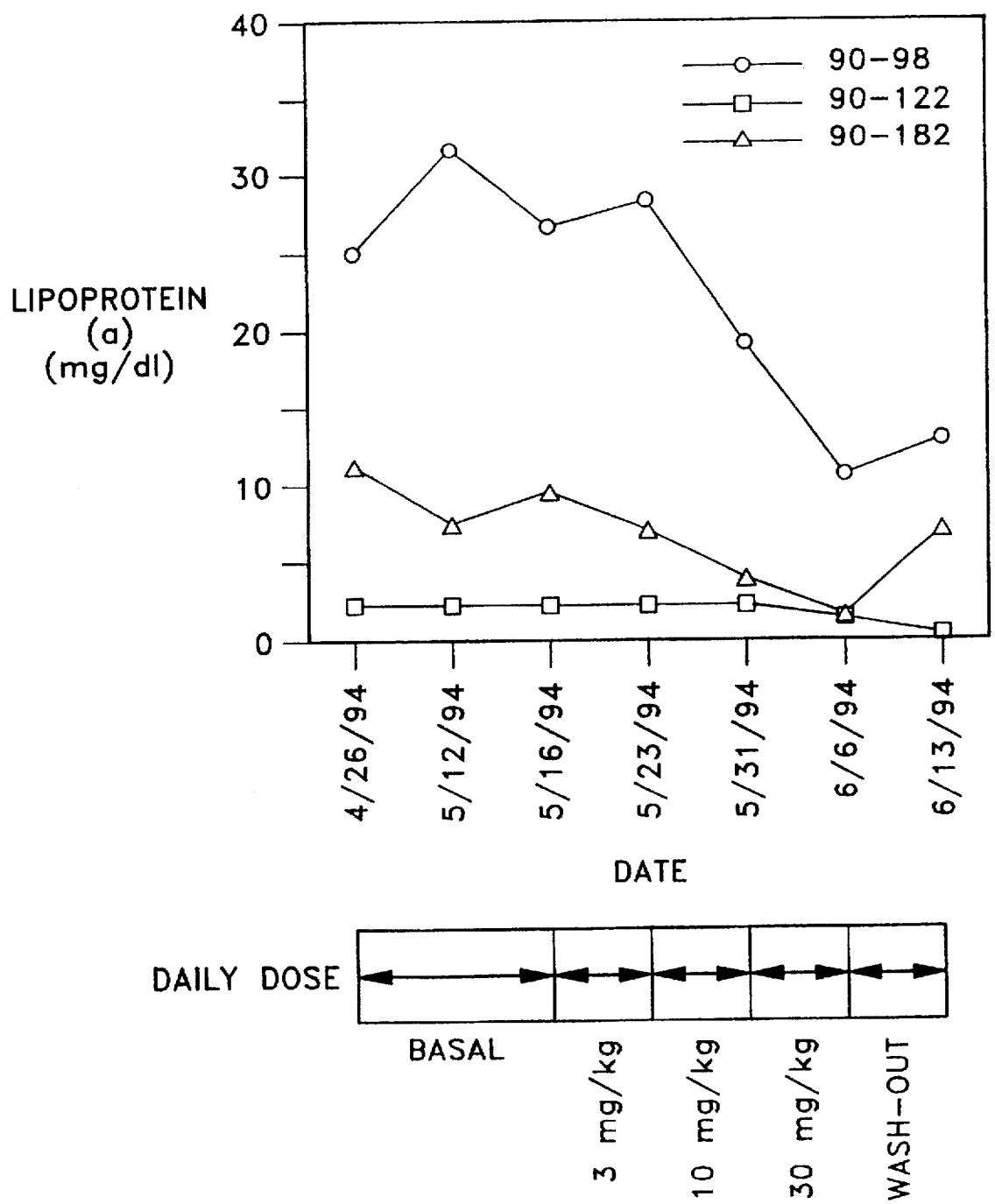
FIG. 5 shows the reduction in Lp(a) levels in monkeys caused by various doses of PD 72953.
Figure 5B:
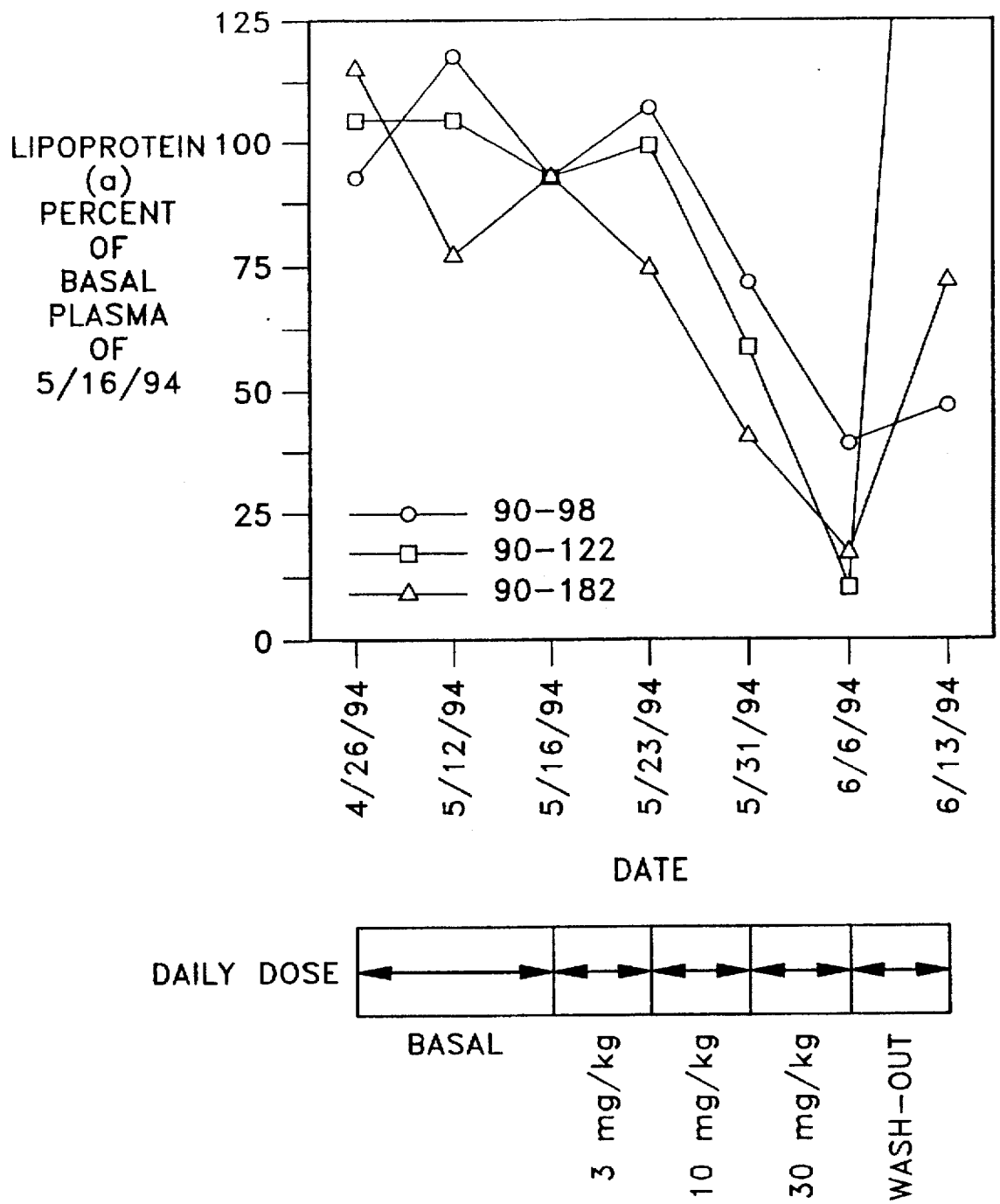

In primates, the Lp(a)-cholesterol contributes to the ascending shoulder of the LDL peak. With progressive treatments, the LDL peak became more symmetrical, possibly reflecting a decrease in Lp(a). Therefore, Lp(a) was measured directly by ELISA (FIG. 5). Direct Lp(a) quantitation demonstrated a dose-dependent reduction in Lp(a) levels, achieving 62%, 83%, and 89% reductions (78±8% average) at the 30-mg/kg Example 1 dose, independent of basal levels in three monkeys (FIG. 5). After a 1-week washout period, Lp(a) approached or exceeded pretreatment levels.

Figure 6:
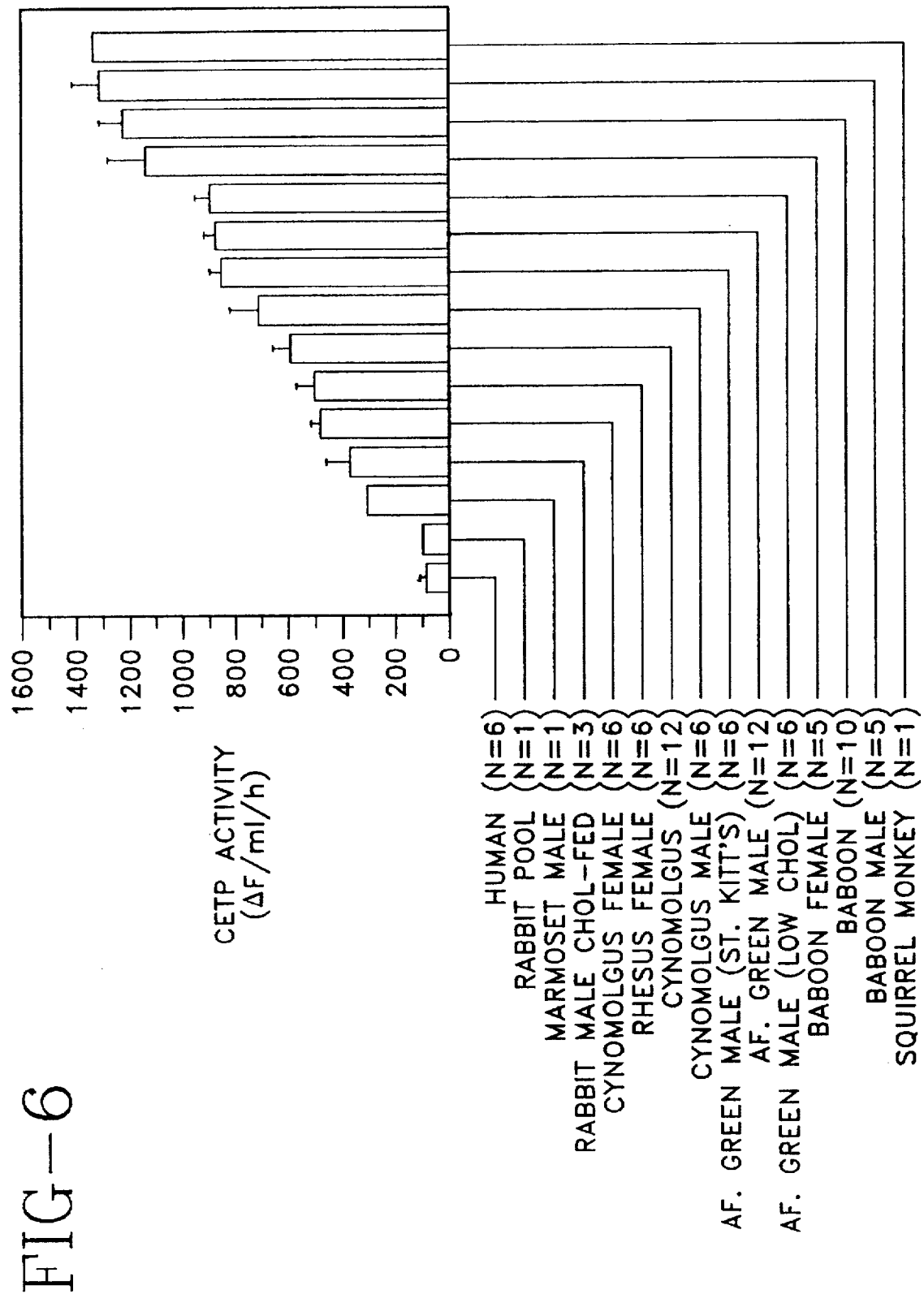
FIG. 6 shows the level of cholesteryl ester transfer protein present in a variety of primate species, including humans.
Figures 7A, 7B:
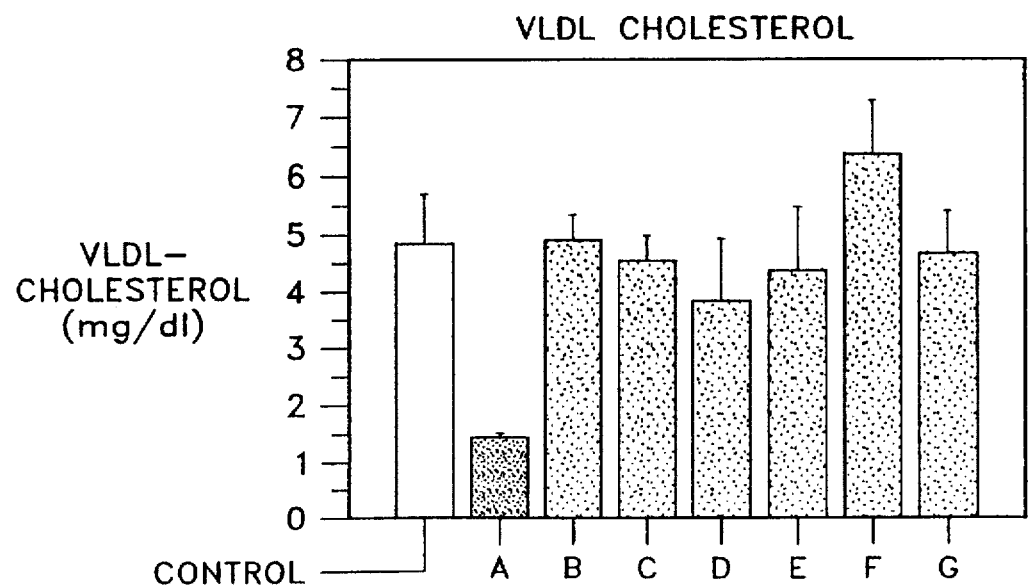
FIG. 7 shows a comparison of the effects on cholesterol in rats caused by several of the invention compounds, and establishes that compound A, PD 72953, is a preferred embodiment of the invention.
Figure 7C:
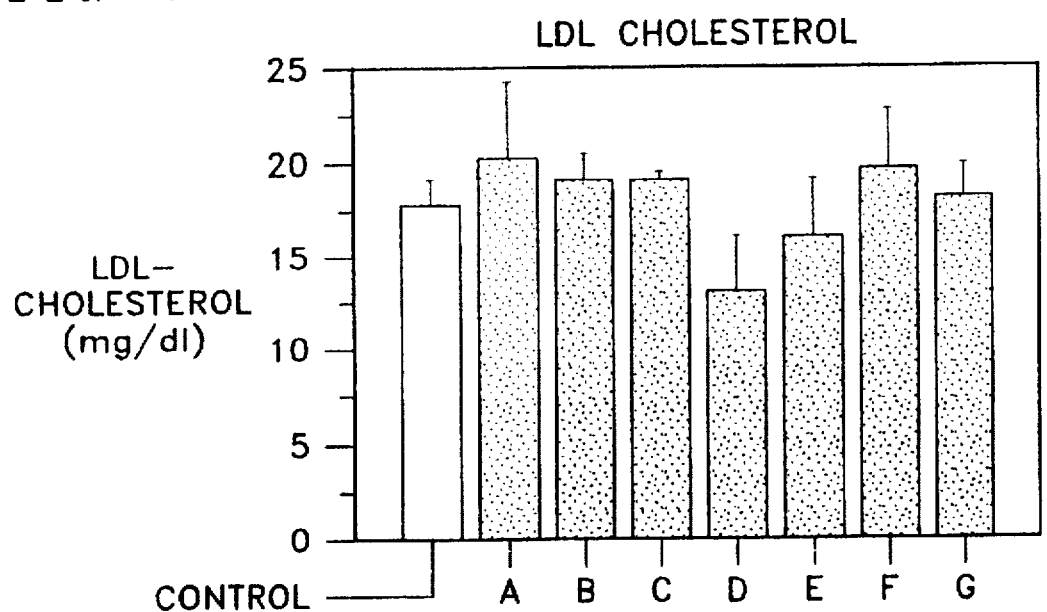
Figure 7D:
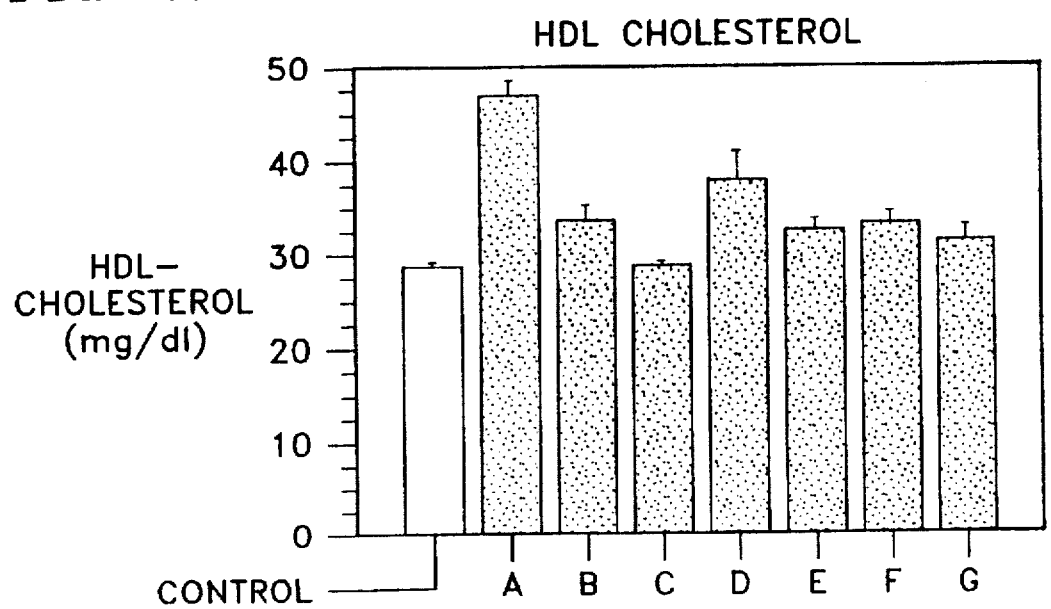
Figure 7E:
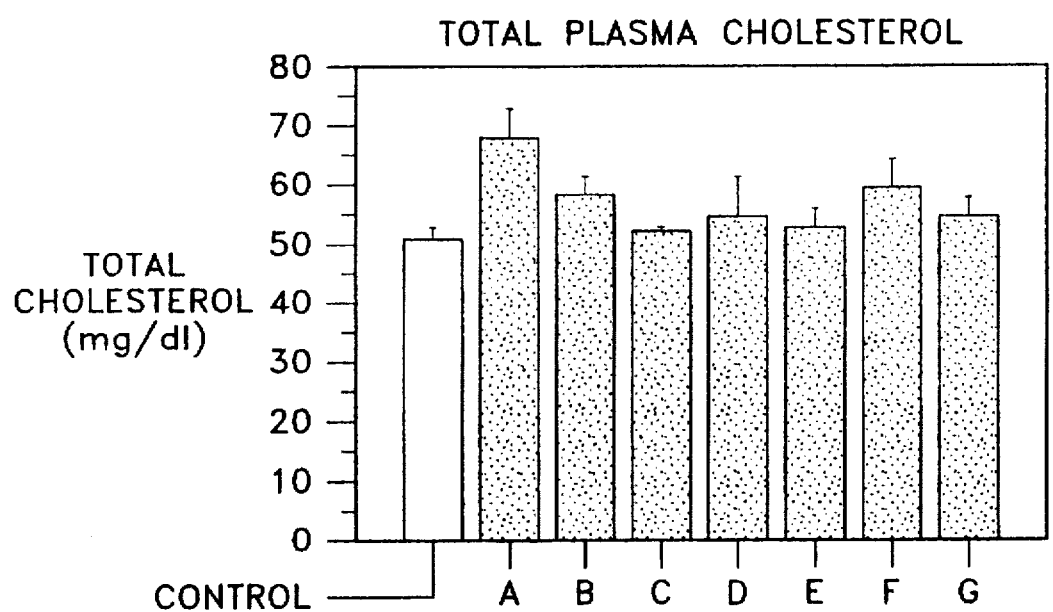
Figure 7F:
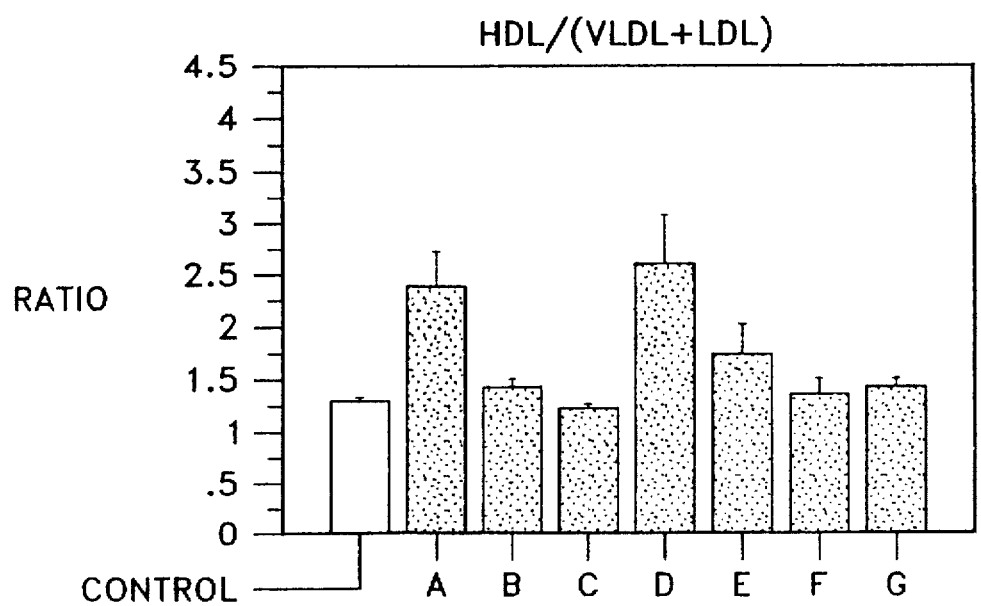
Figure 7G:
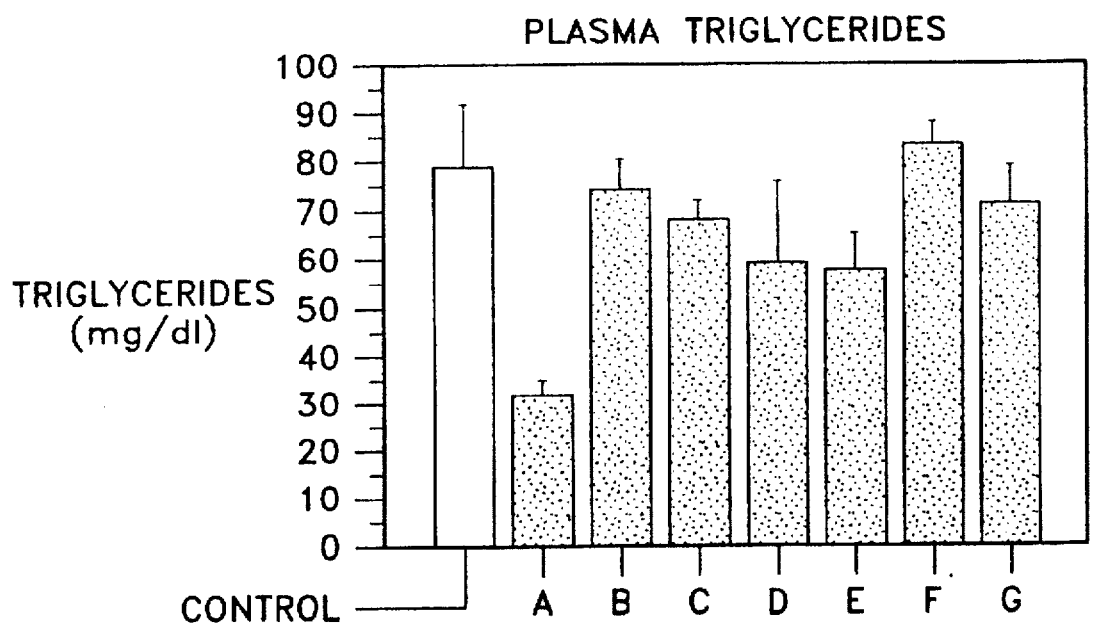
Figure 7H:
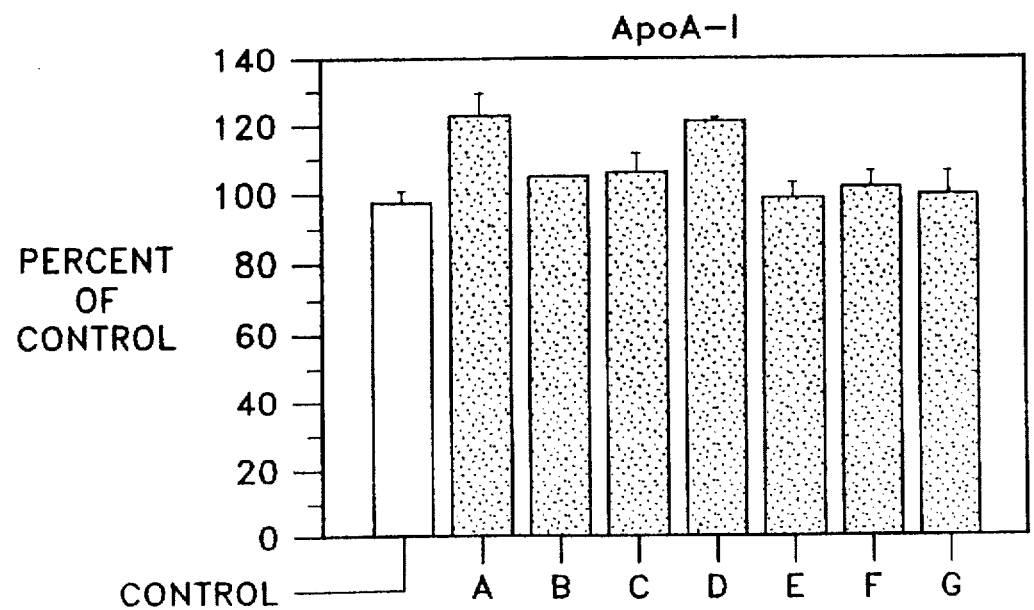
Figure 7I:
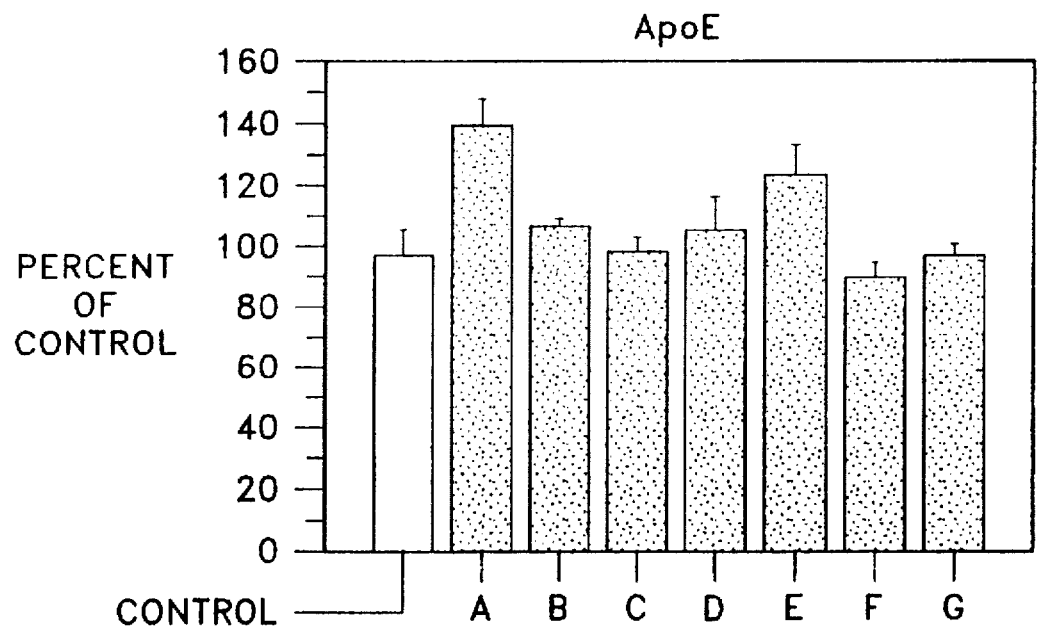
Figure 7J:
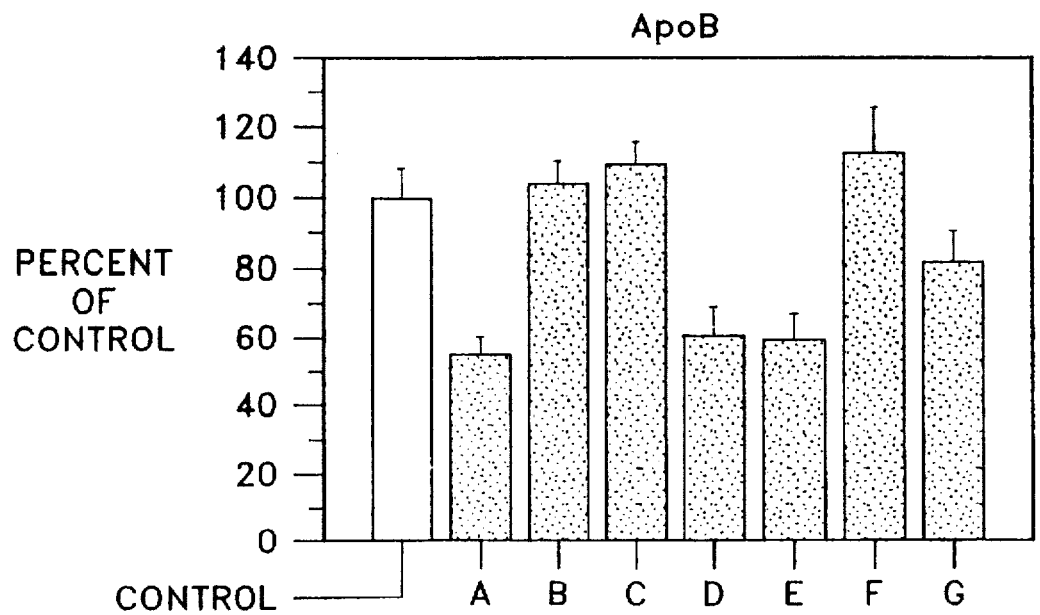
Figure 7K:
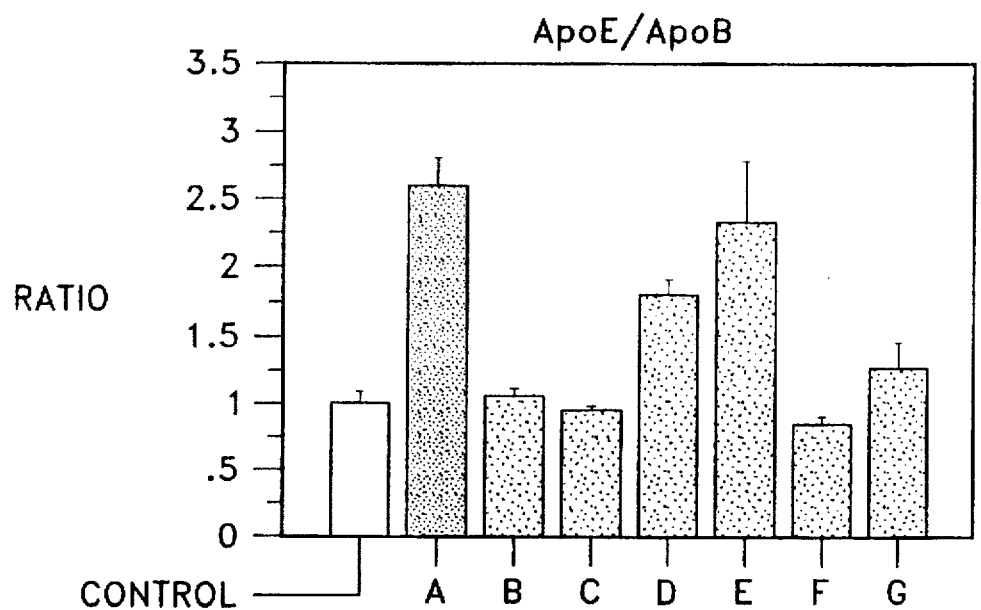
Figure 7L:
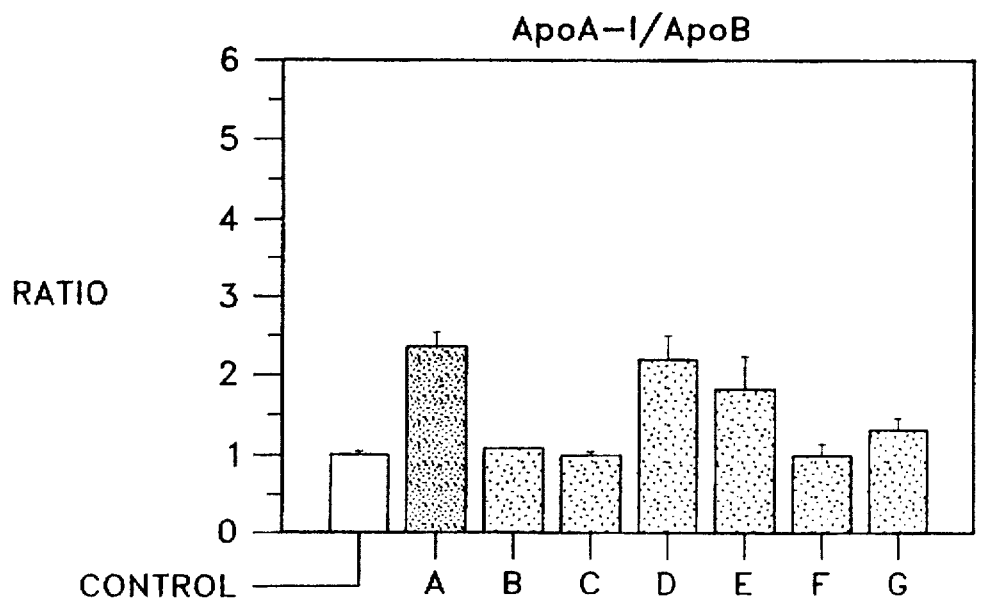
Figure 7M:
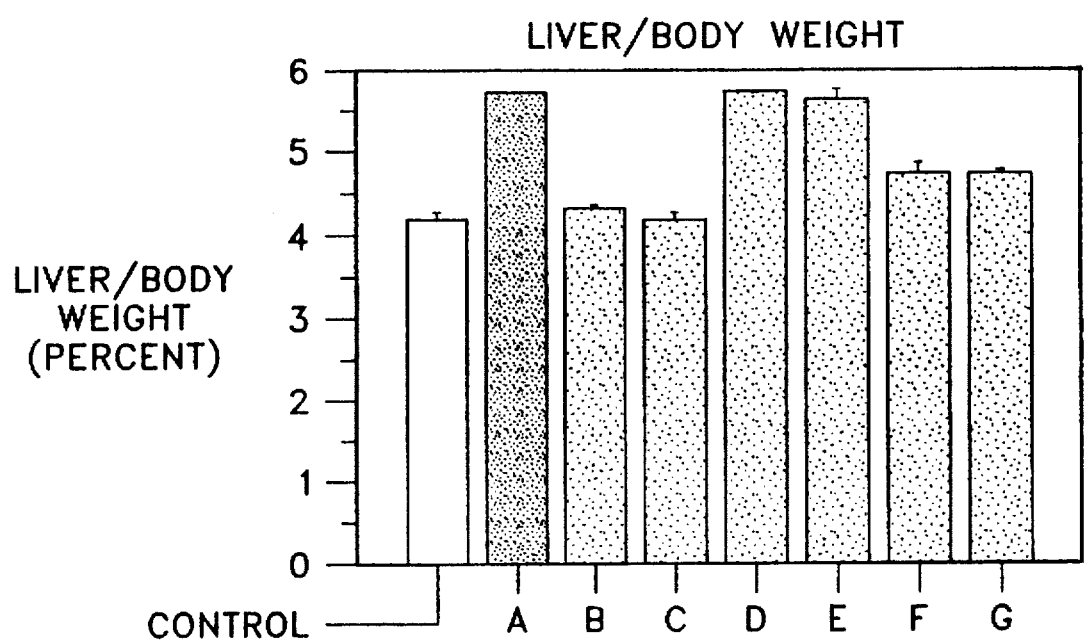

Unlike rats, in which HDL is markedly elevated during treatment with the compound of Example 1, the compound caused a decrease in HDL-cholesterol in the cynomolgus monkey. The reduction of HDL in the cynomolgus monkey may reflect the high level of cholesteryl ester transfer protein (CETP) in this species. Rat plasma has little or no CETP activity. High CETP levels may, therefore, accelerate the rate of transfer of HDL-cholesterol to LDL and LDL precursors, resulting in decreased HDL-cholesterol levels. Analysis of CETP activity levels in rabbits and a variety of primates demonstrate that plasma CETP levels in cynomolgus monkeys are markedly higher (10- to 12-fold) than in humans (FIG. 6). Therefore, an expected result for treatment of humans with the compound of this invention includes lowering of VLDL-, LDL-, and Lp(a)-cholesterol, and elevation of HDL-cholesterol.

FIGS. 1 to 6 show the results of biological evaluation of the compounds of the invention. Results are given for the preferred compound of Example 1. FIG. 1 gives the structure of the preferred compound of Example 1, and identifies it as "PD 72953," which is the term utilized in some of the figures to refer to the Example 1 compound. The reference agent is gemfibrozil, sometimes referred to in the figures as "CI-719."

FIG. 2 shows the effects of the Example 1 compound when administered to chow-fed rats. Male Sprague-Dawley rats were orally dosed daily with carboxymethylcellulose/ tween vehicle, gemfibrozil, or the compound of Example 1 at the indicated concentrations between 6 to 9 AM for 7 days. In one experiment, eight rats in the control group, eight rats in the gemfibrozil group, and eight rats in each of the Example 1 groups dosed at 1, 3, 10, 30, and 100 mg/kg/d were treated for 14 days. Animals were allowed food and water ad libitum and sacrificed by ether inhalation approximately 12 hours after the last dose. Total cholesterol and triglycerides were determined enzymatically. Lipoprotein profiles were determined by quantitative high performance gel chromatography (HPGC). HPGC peak (see FIG. 3 for example) areas plus total plasma cholesterol data were used to determine cholesterol in lipoprotein fractions. Apolipoproteins A-I and E were determined by immunoelectrophoresis. Apolipoprotein B was determined by an immunoturbidometric method. In the 14-day experiment, hepatic carnitine acyltransferase activity was determined as an indication of peroxisomal enzyme activity. This methodology is described by Krause, et al., *Pharmacol. Res.*, 29:345–357 (1994). These data indicate Example 1 causes a dose-dependent increase in this activity, having activation similar to that seen with gemfibrozil at the 100-mg/kg/d dose. Data represents the mean ± SEM for values determined with respect to the control group from nine separate experiments.

Rats were treated as described above for FIG. 2. Plasma was subjected to HPGC to determine cholesterol distribution between lipoproteins. All profiles from each group of eight rats were drawn to the same scale within a group and between the groups. A reference profile of the first rat in the control group is overlaid on each treatment group of eight rats.

HPGC was used to analyze lipoprotein cholesterol profiles in 10 μL plasma from three cynomolgus monkeys (Monkeys 90–98, 90–122, 90–182) prior to, during treatment, and following a 1-week washout of Example 1. During the rising-dose weekly treatment periods, Example 1 at the indicated doses was given daily by oral gavage in a carboxymethylcellulose/tween vehicle between 5 to 6 AM in the fasted state. Bloods were drawn on the indicated dates prior to dosing and in the fasted state. Animals were fed 20 normal monkey chow biscuits, 12 grapes, and 1 banana daily. The profiles of the three basal samples for each monkey were essentially identical, therefore, for each monkey these three profiles were averaged to generate a representative profile. Note that the LDL peak is reduced and more symmetrical as treatment proceeds suggestive of a reduction in Lp(a).

Lp(a) was determined with a commercially available ELISA kit. Plasma samples from each bleed were aliquoted in small volumes (100 μL) and frozen at −70° C. Lp(a) for all plasma samples were determined in the same assay. Data shown in FIG. 5 represent the absolute (top panel) and relative to basal (bottom panel) Lp(a) levels of the three monkeys shown in FIG. 4.

Cholesteryl ester transfer protein (CETP) activity, as shown in FIG. 6, was determined in a variety of primate species and in chow-fed and cholesterol-fed rabbits. CETP activity was determined in whole plasma by determination of the transfer rate of a fluorescent synthetic cholesteryl ester analog contained in microemulsions by the method of Bisgaier, et al., *Lipid Res.*, 34:1625–1634 (1993).

To compare the relative effectiveness of the compound of Example 1 to other compounds of this invention, a 1-week experiment was performed in chow-fed rats. Male Sprague-Dawley rats were orally administered carboxymethylcellulose/tween vehicle or the invention compounds indicated in FIG. 7 (see chart within figure for structures) at 30 mg/kg/d between 6 to 9 AM for 7 days. Animals were allowed food and water ad libitum and sacrificed by ether inhalation approximately 12 hours after the last dose. Plasma triglycerides, plasma total cholesterol, cholesterol distribution between lipoproteins, and apolipoproteins were determined as described previously.

FIG. 7 shows the results of the above test. The figure shows that the preferred compound of Example 1 dramatically lowers plasma triglycerides and VLDL cholesterol, and elevates HDL cholesterol.

The dialkyl ethers have also been shown to increase insulin sensitivity, and as such, are useful for increasing glucose utilization in diabetic animals and to treat diabetes, particularly noninsulin-dependent diabetes mellitus. The invention compounds were evaluated in a standard assay utilizing 3T3-L1 adipocytes, which are particularly responsive to insulin, i.e., sugar uptake can be acutely activated 15- to 20-fold by insulin. The methodology utilized for the assay is described more fully by Frost, et al., *J. Biol. Chem.*, 260:2646–2652 (1985).

Specifically, 3T3-L1 fibroblast cells were obtained from American Type Culture Collection (ATCC, Rockville, Md.). Cells were grown to confluence and differentiated into adipocytes. On Day 0, confluent cells were treated with 167 mm insulin, 0.25 μM dexamethasone, and 0.5 mM methyl isobutylmethyl-xanthine in 10% fetal bovine serum (FBS) containing Dulbecco's Modified Eagle's Medium (DMEM). Two days later, the media was changed to DMEM containing 167 nm insulin and 10% FBS. The media was then switched to 10% DMEM and changed every other day until harvest. The experimental compounds, solubilized in dimethyl sulfoxide, were included in the media on Day 0 and replenished with each media change. Differentiation was assessed by visualizing the accumulation of fat droplets in the cells. Glucose transport was measured by quantitating the incorporation of [$^{14}$C] deoxyglucose in differentiated cells on Day 9, according to the methodology described by Sandouk, et al., *Endocrinology*, 133:352–359 (1993).

Figure 8:
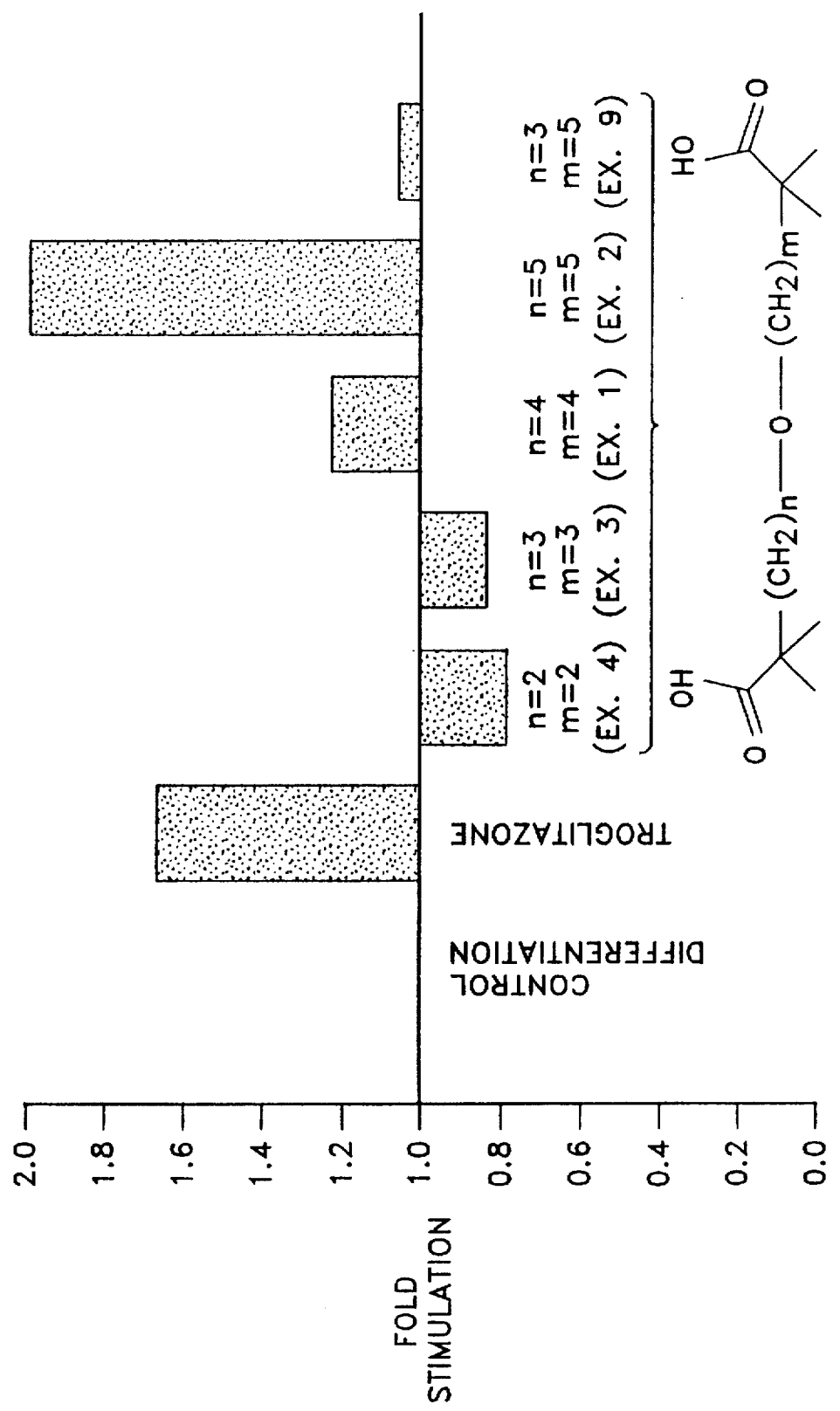
FIG. 8 shows the effect of invention compounds on glucose transport in cells, compared to troglitazone, an agent known to increase glucose utilization in animals.

FIG. 8 shows the results of the cellular evaluation of representative compounds of the invention. Glucose transport was assessed at basal levels, indicative of the expression of the glucose transporter Glut 1 in these cultured adipocytes. Troglitazone, a compound being clinically developed as an agent to increase glucose utilization in animals and humans (described fully in Example 2, U.S. Pat. No. 4,572,912), was included as a reference compound, producing a 70% increase in glucose transport in these cells at 5 μM. This activity of troglitazone is predictive of its insulin-sensitizing actions. Of the invention compounds tested, test compounds of both Example 1 and Example 2 produced a marked increase in glucose transport activity, with the Example 2 compound causing a 2-fold stimulation. The invention compounds were evaluated at 100 μM.

As can be seen from the foregoing data, the dialkyl ethers of this invention are effective at lowering Lp(a), triglycerides, apolipoprotein B, VLDL-cholesterol, and LDL-cholesterol. The compounds also elevate apolipoprotein A-I, apolipoprotein E, HDL-cholesterol, and the HDL/ (VLDL+LDL) ratio. As such, the compounds are useful for treating and preventing vascular disease and noninsulin-dependent diabetes mellitus. A further embodiment of this invention is a method of treating and preventing vascular disease and diabetes comprising administering to a mammal in need of treatment an effective amount of a compound of Formula I. An "effective amount" is the dose required to treat or prevent the vascular disease or diabetes of the mammal. The compounds typically will be administered at a dose of about 50 to about 5000 mg/day, more generally at about 50 to about 2000 mg/day. A commonly employed dosage regimen will be about 50 to about 300 mg administered from one to four times a day. These same dosage levels will be employed for treatment and prevention of vascular disease, as well as for specifically lowering plasma levels of Lp(a) and elevating plasma HDL-cholesterol, and for treating and preventing diabetes.

A further embodiment of this invention are pharmaceutical formulations comprising a compound of Formula I together with a pharmaceutically acceptable excipient, carrier, or diluent. The compounds can be formulated for convenient oral or parenteral administration, with oral delivery being preferred. Typical pharmaceutical carriers and excipients utilized in oral formulations include lactose; sucrose; starches such as corn starch and potato starch; cellulose derivatives such as methyl and ethyl cellulose; gelatins; talc; oils such as vegetable oils, sesame oil, cottonseed oil; and glycols such as polyethylene glycol. Oral preparations typically will be in the form of tablets, capsules, emulsions, solutions, and the like. Controlled release formulations, for example, using a polymeric matrix or an osmotic pump, or the like, can also be utilized. Typical formulations will contain from about 5% to about 95% by weight of the dialkyl ether administered with the excipient or carrier. Flavoring agents such as cherry flavor and orange flavor can be incorporated.

For parenteral administration, the compounds can be formulated with diluents such as isotonic saline, 5% aqueous glucose, and the like, for convenient intramuscular and intravenous delivery. The compounds can also be formulated with waxes and gels in the form of suppositories. The compounds also are well-suited to transdermal delivery, and can be formulated with penetrants and the like in the form of patches. The following example further illustrates typical formulations provided by this invention.

EXAMPLE 10

| Ingredient | Amount |
|---|---|
| 2,2-dimethyl-6-(3-methyl-3-hydroxy-carbonylbutyloxy)hexanoic acid | 1000 g |
| Lactose | 960 g |
| Magnesium Stearate | 40 g |

The ingredients are blended to uniformity and filled into #4 hard gelatin capsules. Each capsule is filled with 200 mg of the blended mixture and contains 100 mg of active dialkyl ether. The capsules are administered to an adult human at the rate of one to three each day to lower plasma Lp(a).

| Ingredient | Amount |
|---|---|
| 2,2-dimethyl-6-(6-methyl-6-ethoxy-carbonylheptyloxy)hexanoic acid | 3000 g |
| Lactose | 750 g |
| Corn Starch | 300 g |
| Gelatin | 120 g |
| Water | 1000 cc |
| Magnesium Stearate | 20 g |

The dialkyl ether, lactose, and 150 g of the corn starch are blended with a solution of the gelatin in the water. The wet granulation is screened, dried, and rescreened. The dried granules are blended with the magnesium stearate and the remaining corn starch, and the mixture is compressed into 698-mg tablets using $^{15}/_{32}$ inch standard concave punches. Each tablet contains 500 mg of dialkyl ether.

| Ingredient | Amount |
|---|---|
| 6,6'-oxybis(2,2-dimethylhexanoic acid) | 4.0 g |
| Polyoxyethylene sorbitan monostearate | 0.1 cc |
| Sodium carboxymethyl cellulose | 0.3 g |
| Complex Magnesium Aluminum Silicate | 0.5 g |
| Sugar | 10 g |
| Glycerin | 2 cc |
| Sodium benzoate | 0.5 g |
| Sodium citrate | 0.2 g |
| Approved red dye | 1 mg |
| Cherry flavor | 0.02 cc |
| Distilled water qs | 100 cc |

The polyoxyethylene sorbitan monostearate can be a product such as polysorbate 60 or Tween 60. The complex magnesium-aluminum silicate is a gel-forming agent. A product such as Veegum H.V. can be used. This substance is hydrated overnight in 10 cc of distilled water. A mixture is prepared from the polyoxyethylene sorbitan monostearate, imitation cherry flavor, 30 cc of distilled water, and the dialkyl ether and passed through a homogenizer. With vigorous stirring, the sugar, glycerin, sodium citrate, sodium benzoate, and sodium carboxymethyl cellulose are added, followed by hydrated complex magnesium-aluminum silicate and a solution of the red dye in 2 cc of water. The resulting suspension is homogenized, adjusted to pH 5.0 with citric acid, and diluted to a final volume of 100 cc with distilled water. A 55-cc oral dosage unit of this suspension contains 200 mg of the dialkyl ether. If desired, the red dye and imitation cherry flavor can be omitted or replaced by other coloring and flavoring agents.

A preferred embodiment of this invention is utilizing the dialkyl ethers to prevent and treat noninsulin-dependent diabetes mellitus and conditions precedent thereto.

Noninsulin-dependent diabetes mellitus (NIDDM), or otherwise referred to as Type II diabetes, is the form of diabetes mellitus which occurs predominantly in adults in whom adequate production of insulin is available for use, yet a defect exists in insulin-mediated utilization and metabolism of glucose in peripheral tissues. Overt NIDDM is characterized by three major metabolic abnormalities: resistance to insulin-mediated glucose disposal, impairment of nutrient-stimulated insulin secretion, and overproduction of glucose by the liver.

People who actually develop NIDDM appear to do so because their B-cells eventually fail to maintain sufficient insulin secretion to compensate for the insulin resistance. Mechanisms responsible for the B-cell failure have not been identified, but may be related to the chronic demands placed on the B-cells by peripheral insulin resistance and/or to the effects of hyperglycemia to impair B-cell function. The B-cell failure could also occur as an independent, inherent defect in "pre-diabetic" individuals.

NIDDM often develops from certain at risk populations, one such population is individuals with polycystic ovary syndrome (PCOS). PCOS is the most common endocrine disorder in women of reproductive age. This syndrome is characterized by hyperandrogenism and disordered gonadotropin secretion producing oligo- or anovulation.

PCOS is associated with profound insulin resistance resulting in substantial hyperinsulinemia. As a result of their insulin resistance. PCOS women are at increased risk to develop NIDDM. Hirsutism, acne, and alopecia, which are commonly found in PCOS women, are clinical manifestations of hyperandrogenism. Menstrual disturbances and infertility are the result of ovulatory dysfunction related to the disordered gonadotropin secretion. Androgen excess, probably by eventual conversion of androgens to estrogen, also plays an important role in disrupting gonadotropin release in PCOS.

NIDDM also develops from the at risk population of individuals with gestational diabetes mellitus (GDM). Pregnancy normally is associated with progressive resistance to insulin-mediated glucose disposal. In fact, insulin sensitivity is lower during late pregnancy than in nearly all other physiological conditions. The insulin resistance is thought to be mediated in large part by the effects of circulating hormones such as placental lactogen, progesterone, and cortisol, all of which are elevated during pregnancy. In the face of the insulin resistance, pancreatic B-cell responsiveness to glucose normally increases nearly 3-fold by late pregnancy, a response that serves to minimize the effect of insulin resistance on circulating glucose levels. Thus, pregnancy provides a major "stress-test" of the capacity for B-cells to compensate for insulin resistance.

Other populations thought to be at risk for developing NIDDM are persons with Syndrome X; persons with concomitant hyperinsulinemia; persons with insulin resistance characterized by hyperinsulinemia and by failure to respond to exogenous insulin; and persons with abnormal insulin and/or evidence of glucose disorders associated with excess circulating glucocorticoids, growth hormone, catecholamines, glucagon, parathyroid hormone, and other insulin-resistant conditions.

Failure to treat NIDDM can result in mortality due to cardiovascular disease and in other diabetic complications including retinopathy, nephropathy, and peripheral neuropathy. For many years treatment of NIDDM has involved a program aimed at lowering blood sugar with a combination of diet and exercise. Alternatively, treatment of NIDDM involved oral hypoglycemic agents, such as sulfonylureas alone or in combination with insulin injections.

In any event, what is required is a method of treating at risk populations such as those with PCOS and GDM in order to prevent or delay the onset of NIDDM thereby bringing relief of symptoms, improving the quality of life, preventing acute and long-term complications, reducing mortality and treating accompanying disorders of the populations at risk for NIDDM. The methods of using the disclosed compounds for treating at risk populations with conditions such as PCOS and GDM to prevent or delay the onset of NIDDM as taught herein meet these objectives.

We claim:

1. A method for elevating plasma HDL-cholesterol comprising administering to a mammal an effective amount of a compound of the formula

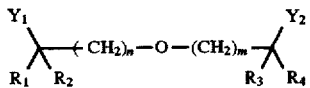   I wherein n and m independently are integers from 2 to 9;

$R_1$, $R_2$, $R_3$ and $R_4$ independently are $C_1$–$C_6$ alkyl, $C_2$–$C_6$ alkenyl, and $R_1$ and $R_2$ together with the carbon to which they are attached, and $R_3$ and $R_4$ together with the carbon to which they are attached, independently can complete a carbocyclic ring having from 3 to 6 carbons;

$Y_1$ and $Y_2$ independently are COOH, CHO, tetrazole, and COOR$_5$ where $R_5$ is $C_1$–$C_6$ alkyl, $C_2$–$C_6$ alkenyl, $C_2$–$C_6$ alkynyl;

and where the alkyl, alkenyl, and alkynyl groups may be substituted with one or two groups selected from halo, hydroxy, $C_1$–$C_6$ alkoxy, and phenyl, and the pharmaceutically acceptable salts thereof.

2. The method of claim 1 employing 6,6'-oxybis(2,2-dimethylhexanoic acid).

3. A method for lowering plasma triglycerides comprising administering to a mammal an effective amount of a compound of the formula

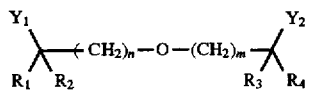   I wherein n and m independently are integers from 2 to 9;

$R_1$, $R_2$, $R_3$, and $R_4$ independently are $C_1$–$C_6$ alkyl, $C_2$–$C_6$ alkenyl, $C_2$–$C_6$ alkynyl, and $R_1$ and $R_2$ together with the carbon to which they are attached, and $R_3$ and $R_4$ together with the carbon to which they are attached, independently can complete a carbocyclic ring having from 3 to 6 carbons;

$Y_1$ and $Y_2$ independently are COOH, CHO, tetrazole, and COOR$_5$ where $R_5$ is $C_1$–$C_6$ alkyl, $C_2$–$C_6$ alkenyl, $C_2$–$C_6$ alkynyl;

and where the alkyl, alkenyl, and alkynyl groups may be substituted with one or two groups selected from halo, hydroxy, $C_1$–$C_6$ alkoxy, and phenyl, and the pharmaceutically acceptable salts thereof.

4. The method according to claim 3 employing 6,6'-oxybis(2,2-dimethylhexanoic acid).

5. A method for lowering LDL-cholesterol comprising administering to a mammal an effective amount of a compound of the formula

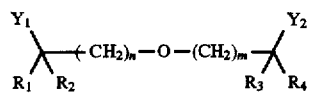   I wherein n and m independently are integers from 2 to 9;

$R_1$, $R_2$, $R_3$, and $R_4$ independently are $C_1$–$C_6$ alkyl, $C_2$–$C_6$ alkenyl, $C_2$–$C_6$ alkynyl, and $R_1$ and $R_2$ together with the carbon to which they are attached, and $R_3$ and $R_4$ together with the carbon to which they are attached, independently can complete a carbocyclic ring having from 3 to 6 carbons;

$Y_1$ and $Y_2$ independently are COOH, CHO, tetrazole, and COOR$_5$ where $R_5$ is $C_1$–$C_6$ alkyl, $C_2$–$C_6$ alkenyl, $C_2$–$C_6$ alkynyl;

and where the alkyl, alkenyl, and alkynyl groups may be substituted with one or two groups selected from halo, hydroxy, $C_1$–$C_6$ alkoxy, and phenyl, and the pharmaceutically acceptable salts thereof.

6. The method according to claim 5 employing 6,6'-oxybis(2,2-dimethylhexanoic acid).

7. A method for lowering VLDL-cholesterol comprising administering to a mammal VLDL-cholesterol lowering amount of a compound of the formula

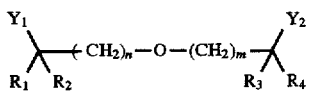

wherein n and m independently are integers from 2 to 9;

$R_1$, $R_2$, $R_3$, and $R_4$ independently are $C_1$–$C_6$ alkyl, $C_2$–$C_6$ alkenyl, $C_2$–$C_6$ alkynyl, and $R_1$ and $R_2$ together with the carbon to which they are attached, and $R_3$ and $R_4$ together with the carbon to which they are attached, independently can complete a carbocyclic ring having from 3 to 6 carbons;

$Y_1$ and $Y_2$ independently are COOH, CHO, tetrazole, and COOR$_5$ where $R_5$ is $C_1$–$C_6$ alkyl, $C_2$–$C_6$ alkenyl, $C_2$–$C_6$ alkynyl;

and where the alkyl, alkenyl, and alkynyl groups may be substituted with one or two groups selected from halo, hydroxy, $C_1$–$C_6$ alkoxy, and phenyl, and the pharmaceutically acceptable salts thereof.

8. The method according to claim 7 employing 6,6'-oxybis(2,2-dimethylhexanoic acid).